U.S. PATENT DOCUMENTS

United States Patent [19]
Gonda et al.
[11] Patent Number: 5,888,477
[45] Date of Patent: *Mar. 30, 1999
[54] USE OF MONOMERIC INSULIN AS A MEANS FOR IMPROVING THE BIOAVAILABILITY OF INHALED INSULIN
[75] Inventors: Igor Gonda, San Francisco; Reid M. Rubsamen, Berkeley; Stephen J. Farr, Or

| | | |
|---|---|---|
| 5,006,343 | 4/1991 | Benson et al. . |
| 5,011,678 | 4/1991 | Wang et al. . |
| 5,167,506 | 12/1992 | Kilis et al. . |
| 5,198,541 | 3/1993 | Elsbach et al. . |
| 5,284,133 | 2/1994 | Burns et al. . |
| 5,320,094 | 6/1994 | Laube et al. . |
| 5,333,106 | 7/1994 | Lanpher et al. . |
| 5,363,842 | 11/1994 | Mishelevich et al. . |
| 5,364,838 | 11/1994 | Rubsamen . |
| 5,394,866 | 3/1995 | Ritson et al. . |
| 5,404,871 | 4/1995 | Goodman et al. . |
| 5,437,267 | 8/1995 | Weinstein et al. . |
| 5,446,020 | 8/1995 | Andy et al. . |
| 5,450,336 | 9/1995 | Rubsamen et al. . |
| 5,497,944 | 3/1996 | Weston et al. . |
| 5,509,404 | 4/1996 | Lloyd et al. . |
| 5,514,646 | 5/1996 | Chance et al. . |
| 5,522,385 | 6/1996 | Lloyd et al. . |
| 5,544,646 | 8/1996 | Lloyd et al. . |
| 5,547,929 | 8/1996 | Anderson . |
| 5,693,608 | 12/1997 | Bechgaard et al. . |
| 5,700,662 | 12/1997 | Chance et al. . |
| 5,743,250 | 4/1998 | Gonda et al. . |

OTHER PUBLICATIONS

Elsbach et al., "Separation and Purification of a Potent Bactericidal/Permeability–Increasing Neutrophil Protein and a Closely Associated Phospholipase $A_2$ from Rabbit Polmorphonuclear Leukocytes," *The Journal of Biological Chemistry*, 254:11000–11009 (1979).

Elsbach et al., "Bactericidal/Permeability Increasing Protein (BPI) of Granulocytes: Structure and Function," *Bacteria–Host Interaction*, 47–60 (1988).

Farley et al., "Antimicrobial Binding of a Radiolabeled Cationic Neutrophil Granule Protein," *Infection and Immunology*, 55:1536–1539 (1987).

Gabay et al., "Antibiotic Proteins of Human Polymorphonuclear Leukocytes," *Proc. Natl. Acad. Sci., USA* 86:5610–5614 (1989).

Gabay et al., "Azurophil–derived Bactericidal Factor(s) from Human Neutrophils," *Clinical Research*, 34:676A 1986).

Gabay et al., "Subcellular Location and Properties of Bactericidal Factors from Human Neutrophils," *J. Exp. Med.*, 186:1407–1421 (1986).

Ganz et al., "Defensins: Natural Peptide Antibiotics of Human Neutrophils," *J. Clin. Invest.*, 76:1427–1435 1985).

Gray et al., "Cloning of the cDNA of a Human Neutrophil Bactericidal Protein," *The Journal of Biological Chemistry*, 264:9505–9509 (1989).

Gray et al. "Cloning of the Gene of the Human Bactericidal/Permeability Increasing Protein and Identification of Structure–Function Relationships," *Clinical Research*, 36:620A (1988).

Gubler et al., "A Simple and Very Efficient Method for Generating cDNA Libraries," *Gene*, 25:263–269 (1983).

Heck et al., Isolation, Characterization, and Amino–Terminal Amino Acid Sequence Analysis of Human Neutrophil Elastase from Normal Donors, *Anal. Biochem.*, 149:153–162 (1985).

Heck., "Isoation, Characterization, and Amino–terminal Amico Acid Sequence Analysis of Human Neutrophil Cathepsin G from normal Donors," *Anal. Biochem.*, 158:217–227 (1986).

Heron, "System for Automated DNA Synthesis," *Am. Biotechnol. Lab.*, 2:52–54, 56, 58–59 (1984).

Hovde et al., "Physiological Effects of a Bactericidal Protein from Human Polymorphonuclear Leudocytes on *Pseudomonas aeruginosa*," *Infect. Immun.*, 52:90–95 (1986).

Hovde et al., "Characterization of a Protein from Normal Human Polymorphonuclear Leukocytes with Bactericidal Activity against *Pseudomonas aeruginosa*," *Infection and Immunity*, 54:142–148 (1986).

Hunkapiller et al., "High–Sensitivity Sequencing with a Gas–Phase Sequenator," *Meth. Enzymol.*, 91:399–413 (1983).

Klein, *Immunology: The Science of Self–Nonself Discrimination*. John Wiley & Sons, NY. p. 101.

Kohler, D., 1990, "Aerosols for systemic treatment," *Lung*, Suppl. :677–84.

Larrick et al., "Complementary DNA Sequence of Rabbit Cap 18—A Unique Lipopolysaccharide Binding Protein," *Biochem. Biophys. Research Communications* 179:170–175 (1991).

Lauber, B.L. et al., 1991, "Deposition, clearance, and effects in the lung," *Journal Aeorsol Medicine* 4:286.

Lauber, B.L. et al., "Preliminary Study of the Efficacy of insulin aerosol delivered by oral inhalation in diabetic patients," 1994, JAMA, 269:2106–2109.

Lehrer et al., Correlation of Binding of Rabbit Granulocyte Peptides to *Candida albicans* with Candidacidal Activity, *Infect. Immun.*, 49:207–211 (1985).

Maniatis et al., (eds.) *Molecular Cloning: A Laboratory Manual*. Cold Spring Harbor Laboratory, Cold Spring Harbor, NY. pp. 188–199 (1982).

Moses, A.C. et al., 1983, "Insulin administed intranasally as an insulin–bile salt aerosos–effectiveness and reproducibility in normal and diabetic subjects," *Diabetes* 32:1040–7.

Muello et al., "The Role of Endotoxin n the Action of the Bactericidal/Permeability Increasing Neutrophil Protein on the Bacterial Envelope," *Clinical Research*, 31:371A (1983).

Nachman et al., "Studies on Isolated Membranes of Azurophil and Specific Granules from Rabbit Polymorphonuclear Leukocytes," *J. Cell Biol.*, 54:133–140 (1972).

Newman, S.P. et al., "Deposition of pressurized aerosols in the human respiratory tract," 1981, Thorax, 36:52–55.

Newman, S.P. et al., "How Should a pressurized β–adrenergic bronchodilator be inhaled?" 1981, Eur. J. Respir. Dis. 62:3–21.

Newman, S.P. et al., "Deposition of pressurized suspension aerosols inhaled through extension devices," 1981, Am. Rev. Respir. Dis. 124:317–320.

Newman, S.P. et al., *Deposition and Effects of Inhalation Aerosols*, Royal Free Hospital, London, (1983) ISBN–91–86058–03–07.

Odeberg et al., Mechanisms for the Microbicidal Activity of Cationic Proteins of Human Granulocytes, *Infect. Immun.*, 14:1269–1275 (1976).

Odeberg et al., "Antibacterial Activity of Cationic Prteins from Human Granulocytes," *J. Clin. Invest.*, 56:1118–1124 (1975).

Okayama et al., "A cDNA Cloning Vector that Permit Expression of cDNA Inserts in Mammalian Cells," *Molec. Cell Biol.*, 3:280–289 (1983).

Olsson et al., "Cationic Proteins of Human Granulocytes. II Separation of the Cationic Proteins of the Granules of Leukemic Myeloid Cells," *Blood*, 44:235–246 (1974).

Ooi et al., "A 25–kDa NH$_2$–terminal Fragment Carries All the Antibacterial Activities of the Human Neutrophil 60–kDa Bactericidal/Permeability–Increasing Protein," *The Journal of Biological Chemistry*, 262:14891–14894 (1987).

Ooi et al., "Endotoxin–Neutralizing Properties of the 25 kD N–Terminal Fragment and a Newly Isolated 30kD C–Terminal Fragment of the 55–60 kD Bactericidal/Permeability–Increasing Protein of Human Neutrophils," *J. Exp. Med.* (1991) 174:649–655.

Pereira et al., "The Ontogeny of a 57–Kd Cationic Antimicrobial Protein of Human Polymorphonuclear Leukocytes: Localization to a Novel Granule Population," *Blood*, 76:825–834 (1990).

Rest et al., "Bactericidal Activity of Specific and Azurophil Granules from Human neutrophils: Studies with Outer–Membrane Mutants of *Salmonella Typhimurium* Lt–2," *Infect. Immun.*, 19:131–137 (1978).

Salvesen et al., "Molecular Cloni ng of Human Cathepsin G: Structural Similarity to Mast Cell and Cytotoxic T Lymphocyte Proteinases," *Biochem*, 26:2289–2293 (1987).

Salzman, R., 1985, "Intranasal aerosolized insulin mixed–meal studies and long–term use in type 1 diabetes," *New England Journal of Medicine* 213:1078–84.

Sciarra et al., 1976, "In Vitro Release of Therapeutically Active Ingredients form Polymer Matrixes," *Journal of Pharmaceutical Sciences* 65(4): 1519–1522.

Selsted et al., "Primary Structures of three Human Neutrophil Defensins" *J. Clin Invest.*, 76:1436–1439 (1985).

Selsted et al., "Primary Structures of Six Antimicrobial Peptides of Rabbit Peritoneal Neurtophils," *J. Biol. Chem.*, 260:4579–4582 (1985).

Selsted et al., "Activity of Rabbit Leukocyte Peptides Against *Candida albicans*," *Infect. Immun.*, 49:202–206 (1985).

Selsted et al., "Purification and Antibacterial Activity of Antimicrobial Peptides of Rabbits Granulocytes," *Infect. Immun.*, 45:150–154 (1984).

Shafer et al., "Cationic Antimicrobial Proteins Isolated from Human Neutrophil Granulocytes in the Presence of Diisopropyl Fluorophosphate," *Infection and Immunity*, 45:29–35 (1984).

Spitznagel et al., "A Monoclonal Antibody that Inhibits the Antimicrobial Action of a 57 KD Cationic Protein of Human Polymorphonuclear Leukocytes," *The Journal of Immunology*, 139:1291–1296 (1987).

Starkey et al., "Neutral Proteinases of Human Spleen," *Biochem. J.*, 155:255–263 (1976).

Suggs et al., "Use of Synthetic Oligonucleotides as Hybridization Probes: Isolation of Clones cDNA Sequences for Human $\beta_2$–microglobulin," *Proc. Natl. Acad. Sci., USA* 78:6613–6617 (1981).

Wallace et al., "The Use of Synthetic Oligonucleotides as Hybridization Probes. II. Hybridization of Oligonucleotides of Mixed Sequence to Rabbit β–globin DNA," *Nuc. Acids Res.*, 9:879–894 (1981).

Weiss et al., "Sensitvity of K1–Encapsulated *Escherichia coli* to Killing by the Bactericidal/Permeability–Increasing Protein of Rabbit and Human Neurtophils," *Infection and Immunity*, 38:1149–1153 (1982).

Weiss et al., The Role of Lipopolysaccharides in the Action of the Bactericidal/Permeability–Increasing Neutrophil Protein on the Bacterial Envelope, *The Journal of Immunology*, 132:3109–3115 (1984).

Weiss et al., "Purification and Characterization of a Potent Bactericidal and Membrane Active Protein from the Granules of Human Polymorphonuclear Leukocytes," Journal of Biological Chemistry, 253:2664–2672 (1978).

Weiss et al., Structural and Immunological Dissection of Highly Conserved Bactericidal/Permeability–Increasing Proteins, *Clinical Research*, 34:537A (1986).

Weiss et al., "Cellular and Subcellular Localization of the Bactericidal/Permeability–Increasing Protein of Neutrophils," *Blood*, 69:652–659 (1987).

Weiss et al., "The Bactericidal/Permeability–Increasing Protein of Neutrophils Retains its Biological Activities after Cleavage by Neutrophil Proteases," *Clinical Research*, 33:567A (1985).

Weiss et al., "Environmental Modulation of Lipopolysaccharide Chain Length Alters the Sensitivity of *Escherichia coli* to the Neutrophil Bactericidal/Permeability–Increasing Protein," *Infection and Immunity*, 51:594–599 (1986).

Weiss et al., "Partial Characterization and Purification of a Rabbit Granulocyte Factor that Increases Permeability of *Escherichia coli*," *The Journal of Clinical Investigation*, 55:33–42 (1975).

Weiss et al., "Role of Charge and Hydrophobic Interactions in the Action of the Bactericidal/Permeability–Increasing Protein of Neutrophils on Gram–negative Bacteria," *Journal of Clinical Investigation*, 71:540–549 (1983).

Wigley, F.M. et al., "Insulin across respiratory mucosae by aerosol delivery," 1971, Diabetes, 20:552–556.

Wilde et al., "Purification and Characterization of Human Neutrophil Peptide 4, a Novel Member of the Defensin Family," *J. Biol. Chem.*, 11200–11203 (1989).

Yoshida, H., et al., 1979, "Absorption of insulin delivered to rabbit trachea using aeroso dosage form," *Journal Pharmaceutical Sciences* 68:670–1.

Young et al., "Efficient Isolation of Genes by Using Antibody Probes," *Proc. Natl. Acad. Sci., USA* 80:1194–1198 (1983).

Remington's Pharmaceutical Sciences, A.R. Gennaro, ed., 1985, Mack Publishing Co.

Salzman, R. 1985, "Intransal aerosolized insulin mixed–meal studies and long–term use in type 1 diabetes," *New England Journal of Medicine* 213:1078–84.

USE OF MONOMERIC INSULIN AS A MEANS FOR IMPROVING THE BIOAVAILABILITY OF INHALED INSULIN

CROSS-REFERENCE TO RELATED APPLICATIONS

This application is a continuation-in-part of application Ser. No. 08/754,423, filed Nov. 22, 1996 now U.S. Pat. No. 5,473,250 issued Apr. 28, 1998 which is a continuation-in-part of earlier filed application Ser. No. 08/549,343, filed Oct. 27, 1995 which application is a continuation-in-part of earlier filed application Ser. No. 08/331,056, filed Oct. 28, 1994 now U.S. Pat. No. 5,672,581 issued Sep. 30, 1997 which is a continuation-in-part of earlier filed application Ser. No. 08/011,281 filed Jan. 29, 1993, now issued U.S. Pat. No. 5,364,838, issued Nov. 15, 1994, each of which is incorporated herein by reference and to which is claimed priority under 35 USC §120.

FIELD OF THE INVENTION

This invention relates generally to a method of, aerosolized drug delivery. More specifically, this invention relates to the controlled intrapulmonary delivery of a monomeric insulin analog alone or in combination with other treatment methodologies which are combined to significantly reduce or eliminate the need for administering insulin by injection.

BACKGROUND OF THE INVENTION

Diabetes Mellitus is a disease affecting approximately 7.5 million people in the United States. The underlying cause of this disease is diminished or absent insulin production by the Islets of Langerhans in the pancreas. Of the 7.5 million diagnosed diabetics in the United States, approximately one-third are treated using insulin replacement therapy. Those patients receiving insulin typically self-administer one or more doses of the drug per day by subcutaneous injection. Insulin is a polypeptide with a nominal molecular weight of 6,000 Daltons. Insulin has traditionally been produced by processing pig and cow pancreas to allow isolation of the natural product. More recently, recombinant technology has made it possible to produce human insulin in vitro. It is the currently common practice in the United States to institute the use of recombinant human insulin in all of those patients beginning insulin therapy.

It is known that most proteins are rapidly degraded in the acidic environment of the GI tract. Since insulin is a protein which is readily degraded in the GI tract, those in need of the administration of insulin administer the drug by subcutaneous injection (SC). No satisfactory method of orally administering insulin has been developed. The lack of such an oral delivery formulation for insulin creates a problem in that the administration of drugs by injection can be both psychologically and physically painful.

In an effort to provide for a non-invasive means for administering insulin, and thereby eliminate the need for hypodermic syringes, aerosolized insulin formulations have been theorized. Aerosolized insulin formulations have been shown to produce insulin blood levels in man when these aerosols are introduced onto nasal or pulmonary membrane. Moses et al. [*Diabetes*, Vol. 32, November 1983] demonstrated that a hypoglycemic response could be produced following nasal administration of 0.5 units/kg. Significant inter-subject variability was noted, and the nasal insulin formulation included unconjugated bile salts to promote nasal membrane penetration of the drug. Salzman et al. [*New England Journal of Medicine*, Vol. 312, No. 17] demonstrated that an intranasal aerosolized insulin formulation containing a non-ionic detergent membrane penetration enhancer was effective in producing a hypoglycemic response in diabetic volunteers. Their work demonstrated that nasal irritation was present in varying degrees among the patients studied. In that diabetes is a chronic disease which must be continuously treated by the administration of insulin and in that mucosal irritation tends to increase with repeated exposures to the membrane penetration enhancers, efforts at developing a non-invasive means of administering insulin via nasal administration have not been commercialized.

In 1971, Wigley et al. [*Diabetes*, Vol 20, No. 8] demonstrated that a hypoglycemic response could be observed in patients inhaling an aqueous formulation of insulin into the lung. Radio-immuno assay techniques demonstrated that approximately 10 percent of the inhaled insulin was recovered in the blood of the subjects. Because the surface area of membranes available to absorb insulin is much greater in the lung than in the nose, no membrane penetration enhancers are required for delivery of insulin to the lungs by inhalation. The inefficiency of delivery seen by Wigley was greatly improved in 1979 by Yoshida et al. [*Journal of Pharmaceutical Sciences*, Vol. 68, No. 5] who showed that almost 40 percent of insulin delivered directly into the trachea of rabbits was absorbed into the bloodstream via the respiratory tract. Both Wigley and Yoshida showed that insulin delivered by inhalation could be seen in the bloodstream for two or more hours following inhalation.

Aerosolized insulin therefore can be effectively given if the aerosol is appropriately delivered into the lung. In a review article, Dieter Kohler [Lung, supplement pp. 677–684] remarked in 1990 that multiple studies have shown that aerosolized insulin can be delivered into and absorbed from the lung with an expected absorption half-life of 15–25 minutes. However, he comments that "the poor reproducibility of the inhaled dose [of insulin] was always the reason for terminating these experiments." This is an important point in that the lack of precise reproducibility with respect to the administration of insulin is critical. The problems associated with the inefficient administration of insulin cannot be compensated for by administering excess amounts of the drug in that the accidental administration of too much insulin could be fatal.

Effective use of an appropriate nebulizer can achieve high efficiency in delivering insulin to human subjects. Laube et al. [*Journal of Aerosol Medicine*, Vol. 4, No. 3, 1991] have shown that aerosolized insulin delivered from a jet nebulizer with a mass median aerodynamic diameter of 1.12 microns, inhaled via a holding chamber at a slow inspiratory flow rate of 17 liters/minute, produced an effective hypoglycemic response in test subjects at a dose of 0.2 units/kg. Colthorpe et al. [*Pharmaceutical Research*, Vol. 9, No. 6, 1992] have shown that aerosolized insulin given peripherally into the lung of rabbits produces a bioavailability of over 50 percent in contrast to 5.6 percent bioavailability seen for liquid insulin dripped onto the central airways. Colthorpe's work supports the contention that aerosolized insulin must be delivered peripherally into the lung for maximum efficiency and that inadvertent central deposition of inhaled aerosolized insulin will produce an effect ten times lower than that desired. Variations in dosing of 10-fold are clearly unacceptable with respect to the administration of most drugs, and in particular, with respect to the administration of insulin.

The present invention endeavors to provide a on-invasive methodology for enhancing the rate and extent of absorption of an aerosolized monomeric insulin analog delivered to a patient.

SUMMARY OF THE INVENTION

Blood glucose levels are rapidly decreased by inhaling a monomeric insulin analog which quickly enters the circulatory system after being inhaled into the lung. The rapid effect is obtained by substantially reducing or eliminating sequestration of drug on the lung tissue after being inhaled. Formulations of monomeric insulin analogs are preferably aerosolized and administered via hand-held, self-contained units which are automatically actuated at the same release point in a patient's inspiratory flow cycle. The release point is automatically determined either mechanically or, more preferably calculated by a microprocessor which receives data from a sensor making it possible to determine inspiratory flow rate and inspiratory volume. The device can measure, provide information to the patient and as such control the inhale-exhale maneuver. Preferably the device is loaded with a cassette comprised of an outer housing which holds a package of individual disposable collapsible containers of a monomeric insulin analog containing formulation for systemic delivery. Actuation of the device forces the insulin analog formulation through a porous membrane of the container which membrane has pores having a diameter in the range of about 0.25 to 3.0 microns, preferably 0.25 to 1.5 microns. The porous membrane is positioned in alignment with a surface of a channel through which a patient inhales air. The flow profile of air moving through the channel is such that the flow at the surface of the channel is less than the flow rate at the center of the channel. The membrane is designed so that it outwardly protrudes at all times or is made flexible so that when an insulin formulation is forced against and through the membrane the flexible membrane protrudes outward beyond the flow boundary layer of the channel into faster moving air. Because the membrane protrudes into the faster moving air of the channel the particles of aerosol formed are less likely to collide allowing for the formation of a burst of fine aerosol mist with uniform particle size.

The dose of insulin analog to be delivered to the patient varies with a number of factors—most importantly the patient's blood glucose level. Thus, the device can deliver all or any proportional amount of the formulation present in the container. If only part of the contents are aerosolized the remainder can be aerosolized at a later time.

Smaller particle sizes are preferred to obtain systemic delivery of insulin analog. Thus, in one embodiment, after the aerosolized mist is released into the channel energy is actively added to the particles in an amount sufficient to evaporate carrier and thereby reduce particle size. The air drawn into the device can be actively heated by moving the air through a heating material which material is pre-heated prior to the beginning of a patient's inhalation. The amount of energy added can be adjusted depending on factors such as the desired particle size, the amount of the carrier to be evaporated, the water vapor content of the surrounding air and the composition of the carrier.

To obtain systemic delivery it is desirable to get the aerosolized formulation deeply into the lung. This is obtained, in part, by adjusting particle sizes. Particle diameter size is generally about one to three times the diameter of the pore from which the particle is extruded. In that it is technically difficult to make pores of 2.0 microns or less in diameter the use of evaporation can reduce particle size to 3.0 microns or less even with pore sizes well above 1.5 microns. Energy may be added in an amount sufficient to evaporate all or substantially all carrier and thereby provide particles of dry powdered insulin or highly concentrated insulin formulation to a patient which particles are uniform in size regardless of the surrounding humidity and smaller due to the evaporation of the carrier.

In addition to adjusting particle size, systemic delivery of insulin is obtained by releasing an aerosolized dose at a desired point in a patient's respiratory cycle. When providing systemic delivery it is important that the delivery be reproducible.

Reproducible dosing of insulin to the patient is obtained by providing for automatic release of formulation in response to a determined inspiratory flow rate and measured inspiratory volume. The method involves measuring for, determining and/or calculating a firing point or drug release decision based on instantaneously (or real time) calculated, measured and/or determined inspiratory flow rate and inspiratory volume points. To obtain repeatability in dosing the formulation is repeatedly released at the same measured (1) inspiratory flow rate and (2) inspiratory volume. To maximize the efficiency of the delivery of the formulation is released at (3) a measured inspiratory flow rate in the range of from about 0.1 to about 2.0 liters/second and (2) a measured inspiratory volume in the range of about 0.1 to about 1.5 liters.

A primary object of the invention is to provide for a method of increasing the rate at which glucose levels can be decreased by delivering a formulation of monomeric insulin analog which is deposited on the lungs and thereafter quickly enters the circulatory system.

Another object is to provide a method of administering a monomeric insulin analog formulation to a patient wherein the formulation is repeatedly delivered to a patient at the same measured inspiratory flow rate (in the range of 0.1 to 2.0 liters/second) and separately determined inspiratory volume (in the range of 0.15 to 1.5 liters).

Another object of the invention is to combine delivery therapies for inhaling an insulin analog with monitoring technologies so as to maintain tight control over the serum glucose level of a patient suffering from diabetes mellitus.

Another object of the invention is to provide a device which allows for the intrapulmonary delivery of controlled amounts of a monomeric insulin analog formulation based on the particular needs of the diabetic patient including serum glucose levels and insulin sensitivity.

Another object of the invention is to provide a means for treating diabetes mellitus which involves supplementing insulin administration using an intrapulmonary delivery means in combination with injections of insulin and/or oral hypoglycemic agents such as sulfonylureas.

Another advantage of the present invention is that the methodology allows the administration of smaller doses of insulin by a convenient and painless route, thus decreasing the probability of insulin overdosing and increasing the probability of safely maintaining desired serum glucose levels.

Another feature of the device of the present invention is that it may be programmed to provide variable dosing so that different doses are delivered to the patient at different times of the day coordinated with meals and/or other factors important to maintain proper serum glucose levels with the particular patient.

Another feature of the invention is that the portable, hand-held inhalation device of the invention can be used in combination with a portable device for measuring serum glucose levels in order to closely monitor and titrate dosing based on actual glucose levels.

Yet another feature of the invention is that the microprocessor of the delivery device can be programmed to prevent overdosing by preventing the formulation release valve from being opened more than a given number of times within a given period of time.

An object of the invention is to provide a container which holds an aerosolizable formulation of monomeric insulin analog which container comprises a porous membrane which protrudes outward in a stationary state or on the application of force forming a convex surface when drug formulation is forced against and through the membrane.

Another object is to provide a method for creating an aerosol of a monomeric insulin formulation which comprises drawing air over a surface of a porous membrane in a channel and forcing formulation against the membrane so as to protrude the membrane through a flow boundary layer into faster moving air of the channel.

Another object of the invention is to adjust particle size by adding energy to the particles in an amount sufficient to evaporate carrier and reduce total particle size.

Another object is to provide a drug delivery device which includes a desiccator for drying air in a manner so as to remove water vapor and thereby provide consistent particle sizes even when the surrounding humidity varies.

Another object is to provide a device for the delivery of aerosols which measures humidity via a solid state hygrometer.

A feature of the invention is that drug can be dispersed or dissolved in a liquid carrier such as water and dispersed to a patient as dry or substantially dry particles.

Another advantage is that the size of the particles delivered will be independent of the surrounding humidity.

Another advantage is that the monomeric insulin analog can be stored in a dry state until just prior to delivery.

These and other objects, advantages and features of the present invention will become apparent to those persons skilled in the art upon reading the details of the structure of the device, formulation of compositions and methods of use, as more fully set forth below.

DETAILED DESCRIPTION OF PREFERRED EMBODIMENTS

Figure 1:
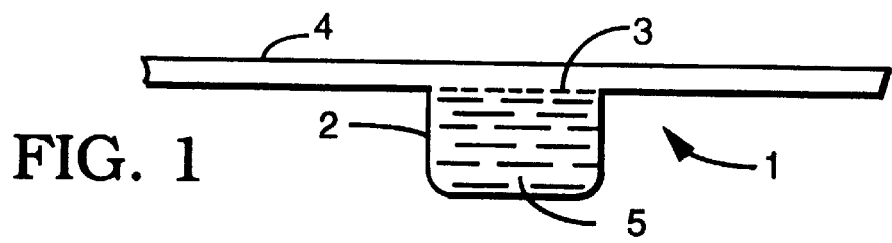
FIG. 1 is a cross-sectional view of a container of the invention.

Before the present method of delivering aerosolized monomeric insulin analog to treat diabetes mellitus and devices, containers and formulations used in the treatment are described, it is to be understood that this invention is not limited to the particular methodology, containers, devices and formulations described, as such methods, devices and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. Thus, for example, reference to "a formulation" includes mixtures of different formulations, reference to "an analog" refers to one or mixtures of insulin analogs, and reference to "the method of treatment" includes reference to equivalent steps and methods known to those skilled in the art, and so forth.

Unless defined otherwise, all technical and scientific terms used herein have the same meaning as commonly understood by one of ordinary skill in the art to which this invention belongs. Although any methods, devices and materials similar or equivalent to those described herein can be used in the practice or testing of the invention, the preferred methods, devices and materials are now described. All publications mentioned herein are incorporated herein by reference for the purpose of describing and disclosing devices, formulations and methodologies which are described in the publication and which might be used in connection with the presently described invention.

Definitions

The term "insulin" shall be interpreted to encompass natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form which includes additional excipients. The insulin is preferably recombinantly produced and may be dehydrated (completely dried) or in solution.

The terms "insulin analog," "monomeric insulin" and the like are used interchangeably herein and are intended to encompass any form of "insulin" as defined above wherein one or more of the amino acids within the polypeptide chain has been replaced with an alternative amino acid and/or wherein one or more of the amino acids has been deleted or wherein one or more additional amino acids has been added to the polypeptide chain or amino acid sequences which act as insulin in decreasing blood glucose levels. In general, the "insulin analogs" of the present invention include "insulin lispro" as disclosed in U.S. Pat. No. 5,547,929, issued Aug. 20, 1996 (incorporated herein by reference) and analogs referred to as "super insulin analogs" wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs which are insulin-like compounds used for the same general purpose as insulin such as insulin lispro i.e., compounds which are administered to reduce blood glucose levels. Monomeric analogs do not bind into groups of molecules such as the hexamers formed by conventional recombinant human insulin.

The term "acceptable serum glucose level" is intended to mean a glucose level above 50 mg/dl and below 300 mg/dl more preferably 80 mg/dl to 200 mg/dl and most preferably about 100 mg/dl. It will be understood by those skilled in the art that levels of about 50 mg/dl are considered low and that levels of about 300 mg/dl are considered high, although acceptable in the sense that these levels are generally not fatal. It is an important aspect of the invention to maintain more acceptable levels which are above the low of 50 mg/dl and below the high of 300 mg/dl with it being more acceptable to deliver doses of insulin so as to keep the patient as close as possible to about 100 mg/dl.

The term "dosing event" shall be interpreted to mean the administration of insulin and/or an insulin analog to a patient in need thereof by the intrapulmonary route of administration which event may encompass one or more releases of formulation from a dispensing device (from one or more containers) over a period of time of 15 minutes or less, preferably 10 minutes or less, and more preferably 5 minutes or less, during which period one or more inhalations are made by the patient and one or more doses of insulin or insulin analog are released and inhaled. A dosing event shall involve the administration of insulin or insulin analog to the patient in an amount of about 1 unit to about 30 units in a single dosing event which may involve the release of from about 1 to about 300 units of insulin from the device.

The term "measuring" describes an event whereby either or both the inspiratory flow rate and inspiratory volume of the patient is measured. The measurement may be used to judge the extent of any inhale-exhale maneuver and/or in order to determine an optimal point in the inspiratory cycle at which to release aerosolized formulation. It is also preferable to continue measuring inspiratory flow during and after any drug delivery and to record inspiratory flow rate and volume before, during and after the release of drug. Such reading makes it possible to determine if formulation was properly delivered to the patient. A microprocessor or other device can calculate volume based on a measured flow rate. When either flow rate or volume becomes known in any manner it can be said to have been determined.

The term "monitoring" event shall mean measuring lung functions such as inspiratory flow, inspiratory flow rate, and/or inspiratory volume so that a patient's lung function as defined herein, can be evaluated before and/or after drug delivery thereby making it possible to evaluate the effect, if any, of delivery on the patient's lung function.

The term "inspiratory flow rate" shall mean a value of air flow rate measured, calculated and/or determined based on the speed of the air passing a given point in a measuring device assuming atmospheric pressure ±5% and a temperature in the range of about 10° C. to 40° C.

The term "inspiratory flow" shall be interpreted to mean a value of air flow calculated based on the speed of the air passing a given point along with the volume of the air that has passed that point with the volume calculation being based on integration of the flow rate data and assuming atmospheric pressure, ±5% and temperature in the range of about 10° C. to about 40° C.

The term "inspiratory volume" shall mean a determined, calculated and/or measured volume of air passing a given point into the lungs of a patient assuming atmospheric pressure ±5% and a temperature in the range of 10° C. to 40° C.

The term "inhaling maximally" shall mean that the patient makes a maximal effort to inhale air into the lungs.

The terms "exhaling the forced vital capacity" and "exhaling maximally" are used interchangeably herein and shall mean making a maximal effort to exhale all air from the lungs, preferably exhaling all air in the lungs but for the residual volume.

The term "inhale-exhale" maneuver shall mean inhaling maximally followed by exhaling maximally. After inhaling maximally the patient can hold the inhaled air for any desired period of time before exhaling maximally or exhale maximally immediately following the maximal inhale.

The term "inspiratory flow profile" shall be interpreted to mean data calculated in one or more events measuring inspiratory flow and cumulative volume, which profile can be used to determine a point within a patient's inspiratory cycle which is preferred for the release of drug to be delivered to a patient. The point within the inspiratory cycle where drug is released may be based on a point within the inspiratory cycle likely to result in the maximum delivery of drug and based and/or on a point in the cycle most likely to result in the delivery of a reproducible amount of drug to the patient at each release of drug. Repeatability of the amount delivered is the primary criterion and maximizing the amount delivered is an important but secondary criterion. Thus, a large number of different drug release points might be selected and provide for repeatability in dosing provided the selected point is again selected for subsequent releases. To insure maximum drug delivery the point is selected within given parameters.

The term "therapeutic index" refers to the therapeutic index of a drug defined as $LD_{50}/ED_{50}$. The $LD_{50}$ (lethal dose, 50%) is defined as the dose of a drug which kills 50% of the tested animals, and the $ED_{50}$ is defined as the effective dose of the drug for 50% of the individuals treated. Drugs with a therapeutic index near unity (i.e. $LD_{50}/ED_{50}$ is approximately equal to 1) achieve their therapeutic effect at doses very close to the toxic level and as such have a narrow therapeutic window, i.e. a narrow dose range over which they may be administered.

The term "liquid formulation" is used herein to describe any pharmaceutically active insulin, analog thereof, or other drug for treating diabetes mellitus by itself or with a pharmaceutically acceptable carrier in flowable liquid form and preferably having a viscosity and other characteristics such that the formulation is aerosolized into particles which are inhaled into the lungs of a patient after the formulation is moved through a porous membrane of the invention. Such formulations are preferably solutions, e.g. aqueous solutions, ethanolic solutions, aqueous/ethanolic solutions, saline solutions and colloidal suspensions. Formulations can be solutions or suspensions of drug in any fluid including fluids in the form of a low boiling point propellant.

The term "formulation" is used to encompass the term "liquid formulation" and to further include dry powders of an insulin analog which is preferably a monomeric insulin analog with or without excipient materials.

The term "substantially" dry shall mean insulin or an analog in a container or in particles of an aerosol which contain less than 10% free water, ethanol or other liquid carrier based on total weight and preferably contains no detectable free liquid carrier.

The terms "lung function" and "pulmonary function" are used interchangeably and shall be interpreted to mean physically measurable operations of a lung including but not limited to (1) inspiratory and (2) expiratory flow rates as well as (3) lung volume. Methods of quantitatively determining pulmonary function are used to measure lung function. Methods of measuring pulmonary function most commonly employed in clinical practice involve timed measurement of inspiratory and expiratory maneuvers to measure specific parameters. For example, forced vital capacity (FVC) measures the total volume in liters exhaled by a patient forcefully from a deep initial inspiration. This parameter, when evaluated in conjunction with the forced expired volume in one second ($FEV_1$), allows bronchoconstriction to be quantitatively evaluated. A problem with forced vital capacity determination is that the forced vital capacity maneuver (i.e. forced exhalation from maximum inspiration to maximum expiration) is largely technique dependent. In other words, a given patient may produce different FVC values during a sequence of consecutive FVC maneuvers. The FEF 25–75 or forced expiratory flow determined over the mid-portion of a forced exhalation maneuver tends to be less technique dependent than the FVC. Similarly, the $FEV_1$ tends to be less technique dependent than FVC. In addition to measuring volumes of exhaled air as indices of pulmonary function, the flow in liters per minute measured over differing portions of the expiratory cycle can be useful in determining the status of a patient's pulmonary function. In particular, the peak expiratory flow, taken as the highest air flow rate in liters per minute during a forced maximal exhalation, is well correlated with overall pulmonary function in a patient with asthma and other respiratory diseases. The present invention carries out treatment by administering drug in a drug delivery event and monitoring lung function in a monitoring event. A series of such events may be carried out and repeated over time.

The term "velocity of the drug" or "velocity of particles" shall mean the average speed of particles of respiratory drug formulation moving from a release point such as a porous membrane or a valve to a patient's mouth. In a preferred embodiment the velocity of the particles is zero or substantially zero in the absence of flow created by patient inhalation.

The term "bulk flow rate" shall mean the average velocity at which air moves through a channel considering that the flow rate is at a maximum in the center of the channel and at a minimum at the inner surface of the channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate.

The term "carrier" shall mean a liquid, flowable, pharmaceutically acceptable excipient material which insulin or insulin analog is suspended in or more preferably dissolved in. Useful carriers do not adversely interact with the insulin analog and have properties which allow for the formation of aerosolized particles preferably particles having a diameter in the range of 0.5 to 3.0 microns when a formulation comprising the carrier and respiratory drug is forced through pores having a diameter of 0.25 to 3.0 microns. Preferred carriers include water, ethanol and mixtures thereof. Other carriers can be used provided that they can be formulated to create a suitable aerosol and do not adversely effect insulin, and insulin analog or human lung tissue.

The term "measuring" describes an event whereby either the inspiratory flow rate or inspiratory volume of the patient is measured in order to determine an optimal point in the inspiratory cycle at which to release aerosolized drug. An actual measurement of both rate and volume may be made or the rate can be directly measured and the volume calculated based on the measured rate. It is also preferable to continue measuring inspiratory flow during and after any drug delivery and to record inspiratory flow rate and volume before, during and after the release of drug. Such reading makes it possible to determine if drug was properly delivered to the patient.

Each of the parameters discussed above is measured during quantitative spirometry. A patient's individual performance can be compared against his personal best data, individual indices can be compared with each other for an individual patient (e.g. $FEV_1$ divided by FVC, producing a dimensionless index useful in assessing the severity of acute asthma symptoms), or each of these indices can be compared against an expected value.

Expected values for indices derived from quantitative spirometry are calculated as a function of the patient's sex, height, weight and age. For instance, standards exist for the calculation of expected indices and these are frequently reported along with the actual parameters derived for an individual patient during a monitoring event such as a quantitative spirometry test.

General Methodology

The invention comprises aerosolizing a formulation of an insulin analog and inhaling the aerosolized formulation into the lungs. Although the inhalation of insulin which results in the insulin entering the circulatory system is known correctly dosing the amount of insulin delivered by inhalation has been problematic. The devices, formulations and methods disclosed herein are useful in solving problems with prior methods. For example, when conventional insulin or human recombinant insulin is delivered to a patient by inhalation the insulin remains on the surface of the lung tissue for a considerable period of time, i.e., does not rapidly enter the circulatory system. The delay between the delivery of the aerosolized insulin and the eventual entry of that insulin into the circulatory system is problematic in that it is desirable to obtain an immediate effect and thereby quickly lower the blood glucose level. If the blood glucose level is not quickly lowered the patient may administer additional insulin which in combination with that already administered will dangerously lower the blood glucose level. The present invention endeavors to solve the problem of insulin sequestration in the lung after delivery by inhalation which is accomplished by the delivery of an insulin analog which rapidly disassociates into its monomeric form. The preferred insulin analog is a monomeric insulin analog which is formulated in accordance with the formulation described in the 1997 PDR at page 1488 (incorporated herein by reference). This preferred insulin analog is also referred to herein as a LysPro insulin analog or simply by the term LysPro which is also referred to herein by the generic name "Humalog." The following provides a description of the conceptual basis of the present invention.

Insulin has been used for over 50 years for the management of diabetes mellitus. Insulin is a naturally occurring hormone which plays a clinical role in glucose metabolism and its absence in patients with Type I Diabetes is a fatal illness unless exogenous insulin is used as part of an insulin replacement therapy program.

Patients have self administered insulin subcutaneously for decades as a means for managing their diabetes. The total daily dose of insulin required by individual patients varies. The availability of portable blood glucose monitors over the last decade has been a significant advancement in that patients can now measure their own blood glucose levels in self dose insulin by injection according to their needs. Many things effect the daily requirement for insulin. These multiple factors require that patients measure blood glucose levels to achieve tight control of their blood glucose.

The Diabetes Control and Complications Clinical Trial (DCCT), a multicenter study designed to evaluate the potential long term beneficial effects of tight blood glucose control, was recently completed. This study demonstrated that insulin acquiring diabetics who maintained their serum glucose were then a specific range over time. Had a significantly reduced complication rate including the avoidance of the consequences of peripheral vascular disease including renal failure chronic diabetic retinopathy and lower extremity problems.

A key element in the attainment of a stable blood glucose level over time involves the administration of subcutaneously administered insulin prior to meal time.

In this way, blood levels of insulin will appear coincident with the increase in blood glucose associated with meal digestion. Recombinant human insulin, which has been available for over more than 10 years, is available in a short acting form (regular insulin) which is appropriate for self administration by injection prior to meal time. Unfortunately, recombinant human insulin must be dosed by injection approximately one half hour prior to meal time in order to insure that a rise in blood glucose does not occur unopposed by exogenous insulin levels.

The acquirement that recombinant human insulin be injected one half hour prior to meal time is burdensome because it requires that patients precisely anticipate the times they will be eating. Eli Lilly has recently introduced Humalog (a recombinant human insulin analog), which is more rapidly absorbed than recombinant human insulin when injected subcutaneously. Because it works more quickly than recombinant human insulin, Humalog can be given just prior to meal time thereby reducing the burden on the patient to plan ahead prior to eating.

Recombinant human insulin in aqueous solution is in a hexameric configuration. In other words, six molecules of recombinant insulin are noncovalently associated in a hexameric complex when dissolved in water in the presence of zinc ions. Studies have demonstrated that hexameric insulin is not rapidly absorbed from the subcutaneous space. In order for recombinant human insulin to be absorbed into circulation, the hexameric form must first associate into dimer and/or a monomeric forms i.e., these forms are required before the material can transit into the blood stream. This requirement for recombinant human insulin to disassociate from hexameric to dimer or mortimeric form prior to absorption is believed to be responsible for the 30 minutes required for a self administer dose of subcutaneous recombinant human insulin to produce a measurable therapeutic blood level.

Although Humalog exists in solution as a hexamer, it very rapidly disassociates into a virtually entirely monomeric form following subcutaneous administration. Clinical studies have demonstrated that Humalog is absorbed quantitatively faster than recombinant human insulin after subcutaneous administration.

Because insulin must be administered frequently in order to allow patients to attain a tight degree of control over their serum glucose, the fact that all insulin products currently need to be delivered by injection is a hindrance to compliance. Results from a DCCT study demonstrate that insulin should ideally be administered 4–6 times each day in order for patients to be likely to achieve an adequate level of blood glucose control to obtain a reduction in complication rate associated with diabetes. A noninvasive method for the delivery of insulin could be beneficial in increasing patient compliance with frequent self administration of insulin throughout the day.

The noninvasive delivery of proteins and peptides has been an elusive goal of the drug delivery industry. Because proteins are rapidly disassociated in the GI tract, oral forms for the delivery of proteins as tablets or capsules have thus far seen limited success. Inhalational drug delivery has been demonstrated to be a viable option for the delivery of proteins and peptides such as insulin via the lung, see U.S. Pat. No. 5,364,838, issued Nov. 15, 1994.

Recent studies have demonstrated that insulin can be reproducibly administered for inhalation to healthy volunteers producing a rapid rise in measurable serum glucose level as well as a rapid fall in blood glucose. U.S. Pat. No. 5,544,646 describes systems for the intrapulmonary delivery of aerosolized aqueous formulations. The system described allows unit dosed packages of aqueous formulated drug to be delivered deep into the lung for systemic effect. U.S. Pat. No. 5,558,085, Intrapulmonary Delivery of Peptide Drugs illustrates how proteins and peptides can be delivered as fine particle aerosols through the lung for systemic effect. U.S. Pat. No. 5,497,763 describes a disposable package for intrapulmonary delivery of aerosolized formulations allowing sealed packets of preformulated drugs such as insulin to be inserted by the patient into aerosolization apparatus for producing fine particle aerosols for deep inhalation.

By quantitatively measuring the inspiratory flow rate and volume during the patients inspiratory maneuver while breathing through the aerosolization system, an optimum point for the delivery of a bolus of aerosolized medication can be determined. U.S. Pat. No. 5,509,404 describes intrapulmonary drug delivery within therapeutically relevant inspiratory flow volume values and illustrates how specific inspiratory flow rate and flow volume criteria can be used to enhance the reproducibility of drugs delivered via the lung for systemic effect. U.S. Pat. No. 5,522,385, Dynamic Particle Size Control for Aerosolized Drug Delivery demonstrates that the parameters of the emitted aerosol can be varied to optimize the delivery of an inhaled aerosol for systemic effect.

U.S. patent application Ser. No. 08/754,423, filed Nov. 11, 1996 now U.S. Pat. No. 5,473,250 issued Apr. 28, 1998 illustrates that recombinant human insulin when delivered as an aerosol for deep inhalation into the lung for systemic effect is sequestered in the lung to a significant degree. This U.S. patent application describes how insulin sequestered within the lung can be made to transit into the systemic circulation if the patient engages in certain specific inspiratory maneuvers following delivery.

Although the reasons for sequestration of insulin in the lung following aerosolized delivery are not known, we speculate that, as with subcutaneous delivery, the disassociation of insulin from hexameric to monomeric form is an important first step prior to the absorption of insulin into the blood stream. A recent controlled experiment conducted by the inventors, quantified the degree to which insulin is sequestered into the lung following aerosolized delivery. In this controlled experiment, the amount of insulin released into the blood stream following aerosol delivery was quantified in cross over fashion with and then without a forced expiratory maneuver following delivery. This study illustrated that a significant amount of insulin is consistently sequestered in the lung following aerosolized delivery.

It is an object of this invention to demonstrate a novel application for Humalog as an insulin analog well suited for pulmonary drug delivery.

It is an object of this invention to demonstrate that Humalog provides unique benefits when delivered via the lung by reducing the degree to which lung sequestration occurs following aerosolized delivery.

It is an object of this invention to demonstrate that by reducing the sequestration of insulin in the lung following aerosolized delivery by delivering Humalog in place of recombinant human insulin that Humalog produces a greater degree of bioavailability as compared to that observed after the delivery of a similar quantity of recombinant human insulin.

It is an object of this invention to demonstrate that by increasing the bioavailability of the delivered insulin analog Humalog that a more reproducible effect on serum blood glucose can be achieved.

It is another object of this invention to demonstrate that the increased bioavailability seen after the delivery of Humalog via aerosolization into the lung results in a more economical approach to the pulmonary drug delivery of insulin than offered by the delivery of recombinant human insulin to the lung via aerosolization.

Although multiple studies have evaluated the feasibility of the delivery of recombinant human insulin via the lung as a fine particle aerosol, no studies have appeared demonstrating that recombinant human insulin is sequestered in the lung following aerosolized delivery. Recently conducted clinical studies demonstrate that significant sequestration of recombinant human insulin is occurring in the lung following aerosol drug delivery. Although this degree of sequestration can be reversed by certain specific pulmonary maneuvers as shown in our copending application, now U.S. Pat. No. 5,473,250 issued Apr. 28, 1998 it will be desirable to substantially reduce or eliminate this sequestration altogether.

Because Humalog rapidly disassociates into monomeric insulin, it is uniquely suited for delivery via the lung.

Inhale/Exhale Maneuver

By delivering a monomeric insulin analog the present invention substantially reduces or eliminates the sequestration of drug on the lung. In situations where sequestration still occurs to some extent it is desirable to carry out an inhale/exhale maneuver. This is accomplished by having the patient inhale maximally and then exhale maximally, i.e. exhale the forced vital capacity of the lungs. The drug delivery device of the present invention preferably includes a sensor which can be mechanical but preferably electronic. The sensor can measure inspiratory flow and volume. Per the present invention the patient is instructed to inhale maximally from the mouthpiece of the drug delivery device so that the inhaled airflow can be measured. In a similar manner the patient is instructed to exhale maximally into the mouthpiece so that the rate and volume of the exhale can be measured. It has been found by carrying out the inhale-exhale maneuver that the rate at which the insulin deposited on lung tissue enters the circulatory system is substantially increased. This is shown dramatically in FIG. 15–19. When the amount of insulin entering the circulatory system increases the glucose level decreases.

From this point forward it should be noted that for brevity purpose the term "insulin" is used to cover all forms of insulin and its analogs including LysPro insulin. When insulin is delivered by any methodology the patient must wait until the insulin has its maximum effect before delivering more insulin to avoid an insulin overdose. Thus, when delivering insulin by inhalation the patient must wait until all or substantially all of the insulin deposited on lung tissue is absorbed into the circulatory system before inhaling additional insulin. If this is not done the patient is dosed with too much insulin such could drive the blood glucose level down to a dangerously low level. Thus, by using the inhale-exhale maneuver of the present invention the patient can more safely and rapidly obtain the desired effect of the administered insulin on the glucose level.

Although an important aspect of the present invention relates to the inhale-exhale maneuver the invention also includes containers, devices and methods which provide a non-invasive means of treating diabetes mellitus in a manner which makes it possible to accurately dose the administration of aerosolized insulin and thereby maintain tight control over serum glucose levels of a patient suffering from the disease. The device of the invention provides a number of features which make it possible to achieve the controlled and repeatable dosing procedure required for treating diabetes.

Specifically, the device is not directly actuated by the patient in the sense that no button is pushed nor valve released by the patient applying physical pressure. On the contrary, the device of the invention provides that aerosolized insulin formulation is released automatically upon receipt of a signal from a microprocessor programmed to send a signal when data is received from a monitoring device such as an airflow rate monitoring device.

A patient using the device withdraws air from a mouthpiece and the inspiratory rate of the patient is measured as is cumulative respiratory volume one or more times in a monitoring event which determines a preferred point in an inhalation cycle for the release of a dose of insulin. Inspiratory flow is measured and recorded in one or more monitoring events for a given patient in order to develop an inspiratory flow profile for the patient. The recorded information is analyzed by the microprocessor in order to deduce a preferred point within the patient's respiratory cycle for the release of insulin with the preferred point being calculated based on the most likely point to result in a reproducible delivery event. The monitoring device continually sends information to the microprocessor, and when the microprocessor determines that the optimal point in the respiratory cycle is reached, the microprocessor actuates the opening of the valve allowing release of insulin.

Accordingly, drug is always delivered at a preprogrammed place in the respiratory flow profile of the particular patient which is selected specifically to maximize reproducibility of drug delivery and peripheral dispersion of the drug. It is pointed out that the device of the present invention can be used to, and actually does, improve the efficiency of drug delivery. However, this is not the critical feature. The critical feature is the enhanced rate at which insulin is brought into the circulatory system and the reproducibility of the release of a tightly controlled amount of drug at a particular point in the inspiratory cycle so as to assure the delivery of a controlled and repeatable amount of drug to the lungs of each individual patient and allow further insulin to be absorbed more quickly if needed.

The combination of automatic control of insulin release, combined with frequent monitoring events in order to calculate the optimal flow rate and time for the release of insulin, combine to provide a repeatable means of delivering insulin to a patient. Because aerosolized insulin formulation is released automatically and not manually, it can predictably and repeatedly be released in the same amount each time to provide a preprogrammed measured amount which is desired. Because dosing events are preferably preceded by monitoring events, the amount of insulin released and/or the point in the inspiratory cycle of the release can be readjusted based on the particular condition of the patient. For example, if the patient's total volume should change, such will be taken into account in the monitoring event by the microprocessor which will readjust the amount and/or point of release of the insulin in a manner calculated to provide for the administration of the same amount of insulin to the patient at each dosing event. Because the inhale-exhale maneuver enhances the rate of absorbtion of insulin into the circulatory system the patient can more quickly control the effect of the insulin on glucose level and determine whether it is necessary to administer additional insulin.

To obtain controlled repeatable dosing a number of factors are preferably considered. Specifically, one should adjust:

(1) The amount of insulin delivered after carrying out the inhale-exhale maneuver of the invention;

(2) the release point within a patient's inspiratory flow rate inside a range of about 0.10 to about 2.0 liters/second preferably about 0.2 to about 1.8 liters per sec. and more preferably 0.15 to 1.7 liters per sec; and within a patient's inspiratory volume of about 0.15 to about 2.0 liters preferably 0.15 to 0.8 liters and more preferably 0.15 to about 0.4 liters;

(3) particle size for systemic delivery in a range of about 0.5 to 6 microns and more preferably 0.5 to about 3 microns;

(4) the concentration of the drug in the carrier in the range of from about 0.01% to about 12.5%;

(5) the amount of heat added to the air about 20 Joules to about 100 Joules and preferably 20 Joules to about 50 Joules per 10 μl of formulation;

(6) the relative volume of air added by patient inhalation per 10 μl of formulation at about 100 ml to 2 l and preferably about 200 ml to 1 liter for evaporation and without evaporation 50–750 ml preferably 200–400 ml;

(7) the rate of vibration of the porous membrane from 575 to 17,000 kilohertz;

(8) pore size to a range of about 0.25 to about 6.0 microns in diameter preferably 0.5 to 3 microns and more preferably 1–2 microns;

(9) viscosity of the formulation to a range of from about 25% to 1,000% of the viscosity of water;

(10) extrusion pressure in a range of about 50 to 600 psi and preferably 100 to 500 psi;

(11) ambient temperature to 15° C. to 30° C. and ambient pressure between 1 atmosphere and 75% of 1 atmosphere;

(12) the ratio of liquid carriers to each other to be consistent;

(13) the solubility of drug to carrier to obtain a high concentration of insulin in the carrier;

(14) the desiccator to maximize removal of water vapor from air;

(15) the shape of the pore opening to be circular in diameter and a conical in cross-section with the ratio of the diameter of the small to large end of the cone being about to ½ to ½₀, and the shape of the porous membrane to an elongated oval;

(16) the thickness of the membrane to 5 to 200 microns; preferably 10–50 microns;

(17) the membrane to have a convex shape or to be flexible so that it protrudes outward in a convex shape beyond the flow boundary layer when formulation is forced through it, and

(18) the firing point to be at substantially the same point at each release for the parameters (1–17), i.e., each release of drug is at substantially the same point so as to obtain repeatability of dosing.

There is considerable variability with respect to the amount of insulin which is delivered to a patient when the insulin is being administered by injection.

Patients requiring the administration of injectable insulin use commercial insulin which is prepared in concentrations of 100 units per milliliter, although higher concentrations up to about 500 units per milliliter can be obtained. It is preferable to use the more highly concentrated insulin in connection with the present invention. If insulin containing 500 units of insulin per milliliter is used and a patient is administering 5 units, then the patient will only need to administer 0.01 milliliters of the concentrated insulin to the lungs of the patient to achieve the desired dose.

The symptoms of diabetes can be readily controlled with the administration of insulin. However, it is extremely difficult, and probably impossible, to normalize the blood sugar throughout a 24-hour period utilizing traditional insulin therapy given as one or two injections per day. It is possible to more closely approach normalized blood sugar levels with the present invention. Improvements are obtained by smaller, more frequent dosing and by timing dosing relative to meals, exercise and sleep.

The precise amount of insulin administered to a patient varies considerably depending upon the degree of the disease and the size of the patient. A normal-weight adult may be started on about a 15–20 units a day in that the estimated daily insulin production rate in non-diabetic subjects of normal size is approximately 25 units per day. It is preferable to administer approximately the same quantity of insulin for several days before changing the dosing regime except with hypoglycemic patients for which the dose should be immediately decreased unless a clearly evident nonrecurrent cause of hypoglycemia (such as not eating, i.e., missing a typical meal) is present. In general, the changes should not be more than five to ten units per day. It is typical to administer about two-thirds of the total insulin daily dosage before breakfast and administer the remainder before supper. When the total dosage reaches 50 or 60 units per day, a plurality of smaller doses are often required since peak action of insulin appears to be dose related, i.e., a low dose may exhibit maximal activity earlier and disappear sooner than a large dose. All patients are generally instructed to reduce insulin dosage by about 5 to 10 units per day when extra activity is anticipated. In a similar manner, a small amount of extra insulin may be taken before a meal that contains extra calories or food which is not generally eaten by the diabetic patient. The inhalation device of the present invention is particularly useful with respect to providing such small amounts of additional insulin.

Several types of insulin formulations are commercially available. When larger doses of insulin must be administered at a single point in time, it may be preferable to administer intermediate or long-acting insulin formulations. Such formulations release some insulin immediately and provide a more sustained release of the remainder of the insulin over time. Such formulations are described further below in the "Insulin Containing Formulations" section.

When administering insulin using the inhalation device of the present invention, the entire dosing event can involve the administration of anywhere from one to 25 units, but more preferably involves the administration of approximately five to ten units. The entire dosing event may involve several inhalations by the patient with each of the inhalations being provided with multiple bursts of insulin from the device. For example, the device can be programmed so as to release enough insulin so that approximately one unit of insulin is delivered to the patient per inhalation or 0.33 units of insulin per burst with three bursts being delivered per inhalation. If ten units are to be delivered, the ten units are delivered by releasing 33 bursts in ten different inhalations. Such a dosing event should take about 1–2 minutes to deliver 10 units of insulin. Since only small amounts are delivered with each burst and with each inhalation, even a complete failure to deliver insulin with a given inhalation or burst is not of great significance and will not seriously disturb the reproducibility of the dosing event. Further, since relatively small amounts are delivered with each inhalation and/or burst, the patient can safely administer an additional unit or two of insulin without fear of overdosing.

There is a differential between the amount of insulin actually released from the device and the amount of insulin actually delivered to the patient. The present device is two to ten times more efficient than conventional inhalation devices (i.e., MDIs or metered dose inhalers) which have an efficiency as low as 10% meaning that as little as 10% of the released insulin may actually reach the circulatory system of the patient. The efficiency of the delivery will vary somewhat from patient to patient and should be taken into account when programming the device for the release of insulin.

One of the difficulties with aerosolized delivery of insulin is that the patient and/or the caregiver cannot determine precisely how much insulin has entered the circulatory system. Accordingly, if the patient has been dosed with what is believed to be an adequate amount of aerosolized insulin and the glucose level remains high one might assume that the aerosolized dose was not properly delivered. For example, the insulin might have been improperly delivered against the patient's mouth surfaces or throat where it will not be absorbed into the circulatory system. However, it may be that the insulin is properly delivered to the lung (e.g., provided on the outer peripheral areas of the lung) but has not yet migrated into the circulatory system. The present invention provides a mechanism for more quickly bringing the insulin deposited on lung tissue into the circulatory system. This method involves the inhale-exhale maneuver whereby the patient inhales maximally and then exhales maximally. The result of carrying out this maneuver is graphically shown in FIGS. 15–19. Specifically, referring to FIG. 15 the amount of insulin in the blood plasma in terms of microunits per milliliter is plotted over time in minutes. An aerosolized dose of insulin is delivered at zero time. At 20 minutes and 40 minutes the patient is instructed to carry out the inhale-exhale maneuver of the invention. As can be seen in the graph, just after 20 minutes in time the plasma level of insulin spikes dramatically. The same result is seen just after 40 minutes. After both spikes in the insulin level the plasma glucose level is shown to be reduced.

Figure 16:
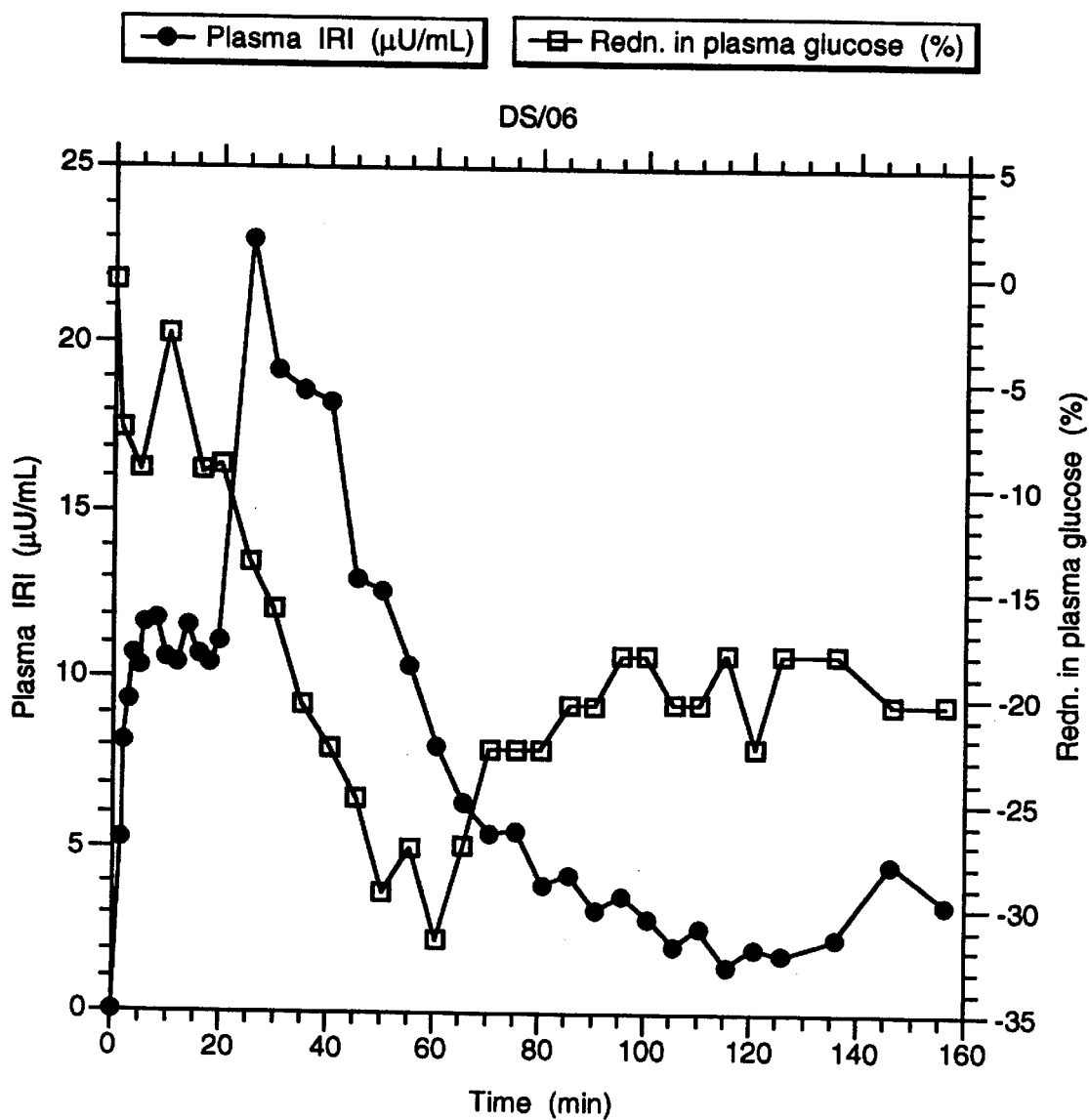
FIG. 16 is a graph plotting the amount of insulin and glucose in plasma over time.
Figure 17:
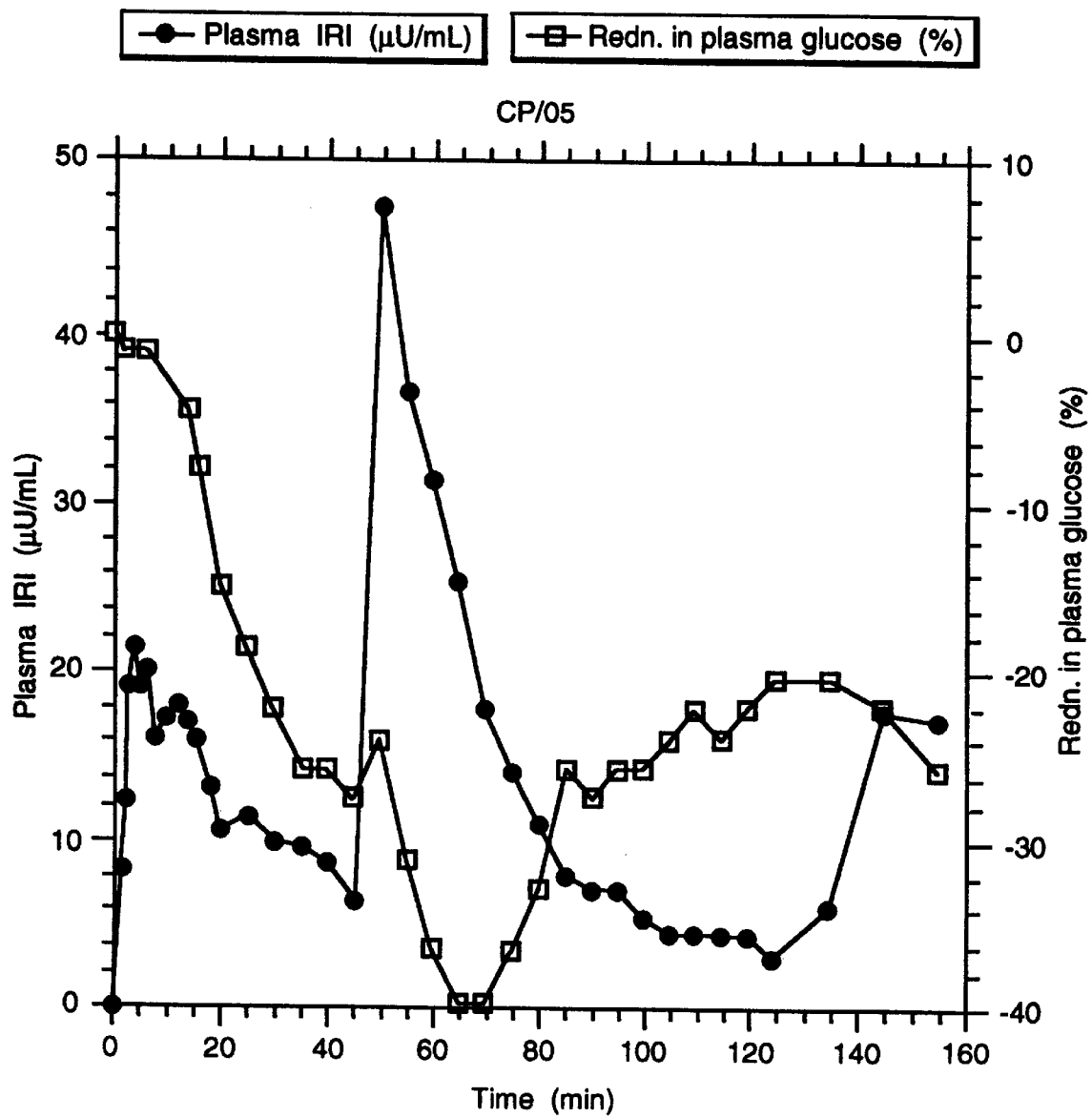
FIG. 17 is a graph plotting the amount of insulin and glucose in plasma over time.
Figure 18:
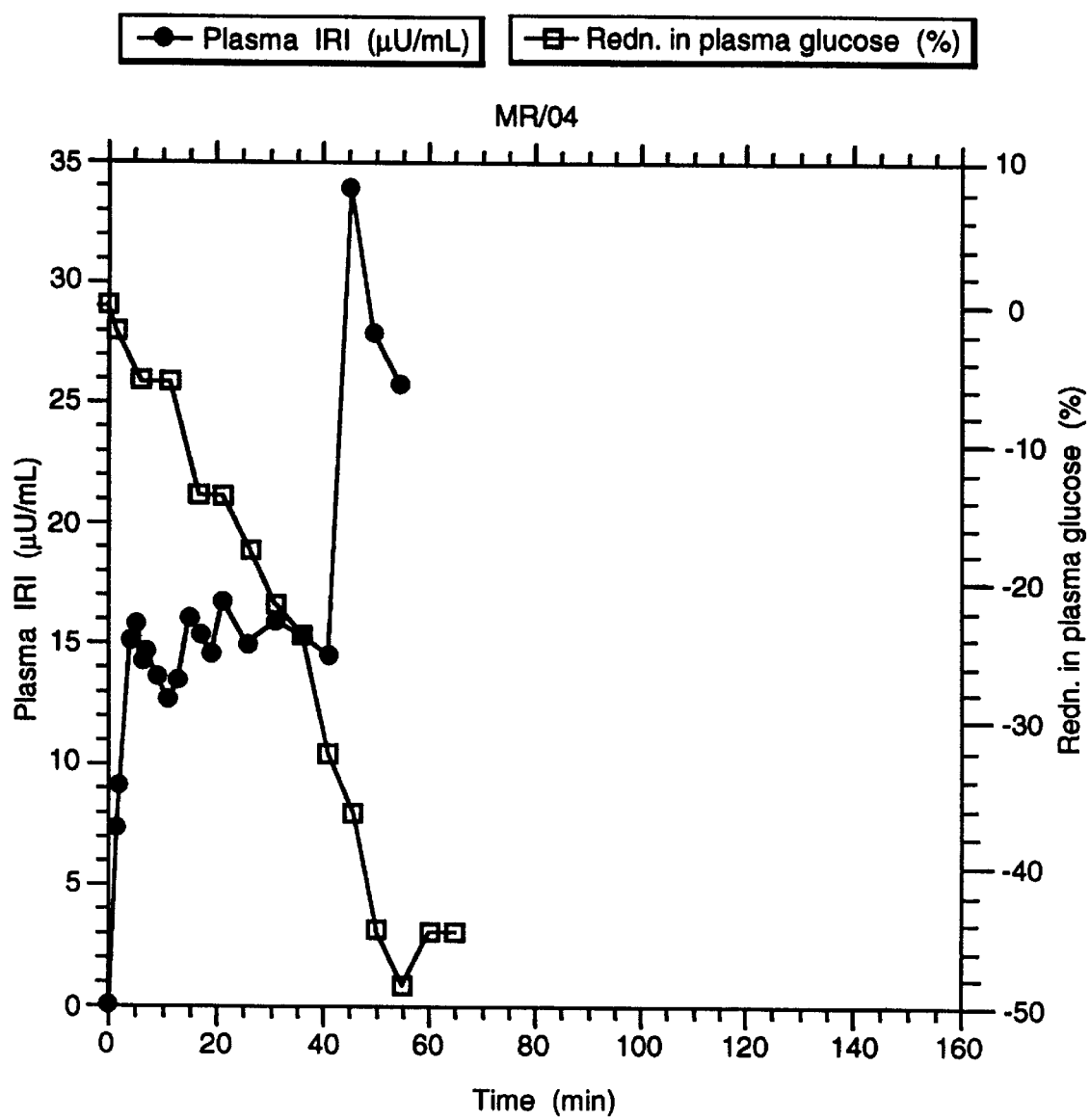
FIG. 18 is a graph plotting the amount of insulin and glucose in plasma over time.
Figure 19:
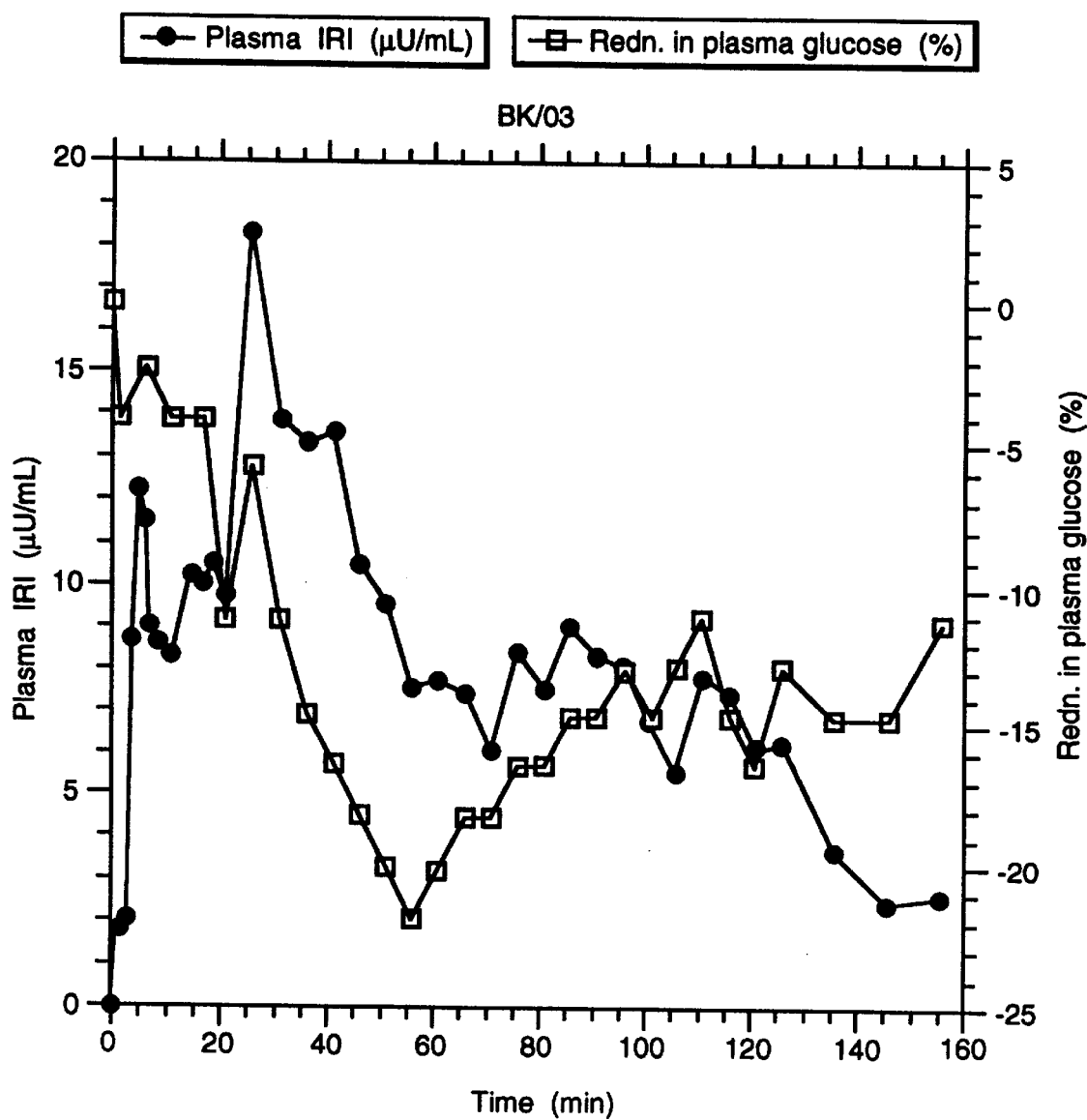
FIG. 19 is a graph plotting the amount of insulin and glucose in plasma over time.

In FIG. 16 a similar graph is shown where the patient is instructed to carry out the inhale-exhale maneuver at 20 minutes after the delivery of insulin. As shown, shortly after the maneuver is performed the amount of insulin found in the plasma spikes dramatically. In FIG. 17 the inhale-exhale maneuver is performed at 40 minutes after delivery. Again, there is shown a dramatic increase in the amount of insulin found in the plasma after the performance of the inhale-exhale maneuver. Similar results are shown in FIG. 18 at the 40 minute point. FIG. 19 also shows the delivery of insulin at the zero point in time. In FIG. 19 the patient carries out the inhale-exhale maneuver at 20 minutes after delivery. Shortly after the maneuver is performed the amount of insulin in the plasma dramatically increases. Per FIG. 19 the maneuver is not performed at the 40 minute interval and, as can be seen, there is no increase in the amount of insulin found in the plasma. Thus, the FIGS. 15–19 clearly demonstrate that the carrying out of the inhale-exhale maneuver of the invention increases the rate at which insulin is moved from the lung tissue into the circulatory system of the patient.

Obese patients are generally somewhat less sensitive to insulin and must be provided with higher doses of insulin in order to achieve the same effect as normal weight patients. Dosing characteristics based on insulin sensitivity are known to those skilled in the art and are taken into consideration with respect to the administration of injectable insulin. The present invention makes it possible to vary dosing over time if insulin sensitivity changes and/or if user compliance and/or lung efficiency changes over time.

Based on the above, it will be understood that the dosing or amount of insulin actually released from the device can be changed based on the most immediately prior monitoring event wherein the inspiratory flow of a patient's inhalation is measured. The amount of insulin released can also be varied based on factors such as timing and timing is, in general, connected to meal times, sleep times and, to a certain extent, exercise times. Although all or any of these events can be used to change the amount of insulin released from the device and thus the amount of insulin delivered to the patient, ultimately, the amount released and delivered to the patient is based on the patient's serum glucose levels. It is important to maintain the serum glucose levels (true) of the patient within acceptable levels (greater than 60 mg/dl and less than 125 mg/100 ml and most preferably to maintain those levels at about 80 mg/100 ml.

Variations in doses are calculated by monitoring serum glucose levels in response to known amounts of insulin released from the device. If the response in decreasing serum glucose level is higher than with previous readings, then the dosage is decreased. If the response in decreasing serum glucose level is lower than with previous readings, then the dosing amount is increased. The increases and decreases are gradual and are preferably based on averages (of 10 or more readings of glucose levels after 10 or more dosing events)

and not a single dosing event and monitoring event with respect to serum glucose levels. The present invention can record dosing events and serum glucose levels over time, calculate averages and deduce preferred changes in administration of insulin.

As another feature of the invention, the device can be programmed so as to prevent the administration of more than a given amount of insulin within a given period of time. For example, if the patient normally requires 25 units per day of insulin, the microprocessor of the inhalation device can be programmed to prevent further release of the valve after 35 units has been administered within a given day. Setting a slightly higher limit would allow for the patient to administer additional insulin, if needed, due to larger than normal meals and/or account for misdelivery of insulin such as due to coughing or sneezing during an attempted delivery.

The ability to prevent overdosing is a characteristic of the device due to the ability of the device to monitor the amount of insulin released and calculate the approximate amount of insulin delivered to the patient based on monitoring given events such as airflow rate and serum glucose levels. The ability of the present device to prevent overdosing is not merely a monitoring system which prevents further manual actuation of a button. As indicated above, the device used in connection with the present invention is not manually actuated, but is fired in response to an electrical signal received from a microprocessor. Applicant's device does not allow for the release of insulin merely by the manual actuation of a button to fire a burst of insulin into the air.

The microprocessor of applicant's invention can be designed so as to allow for an override feature which would allow for the administration of additional insulin. The override feature could be actuated in an emergency situation. Alternatively, the override feature could be actuated when the device is electronically connected with a serum glucose level monitoring device which determines that serum glucose levels increase to dangerously high levels.

The microprocessor of applicant's invention will preferably include a timing device. The timing device can be electrically connected with visual display signals as well as audio alarm signals. Using the timing device, the microprocessor can be programmed so as to allow for a visual or audio signal to be sent when the patient would be normally expected to administer insulin. In addition to indicating the time of administration (preferably by audio signal), the device can indicate the amount of insulin which should be administered by providing a visual display. For example, the audio alarm could sound alerting the patient that insulin should be administered. At the same time, the visual display could indicate "five units" as the amount of insulin to be administered. At this point, a monitoring event could take place. After completion of the monitoring event, administration would proceed and the visual display would continually indicate the remaining amount of insulin which should be administered. After the predetermined dose of five units had been administered, the visual display would indicate that the dosing event had ended. If the patient did not complete the dosing event by administering the stated amount of insulin, the patient would be reminded of such by the initiation of another audio signal, followed by a visual display instructing the patient to continue administration.

Additional information regarding dosing with insulin via injection can be found within Harrison's—Principles of Internal Medicine (most recent edition) published by McGraw Hill Book Company, New York, incorporated herein by reference to disclose conventional information regarding dosing insulin via injection.

Drug Delivery with Disposable Container

FIG. 1 is a cross-sectional view of a container 1 of the invention which is shaped by a collapsible wall 2. The container 1 has an opening covered by a flexible porous membrane 3 which is covered by a removable layer 4. The membrane 3 may be rigid and protrude upward in a convex configuration away from the formulation 5. When the layer 4 is removed the wall 2 can be collapsed thereby forcing the insulin formulation 5 against the flexible porous membrane 3 which will then protrude outward in a convex shape.

Figure 2:
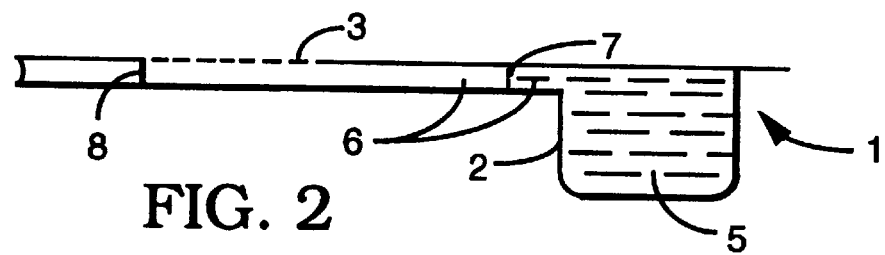
FIG. 2 is a cross-sectional view of a preferred embodiment of a container of the invention.

FIG. 2 is a cross-sectional view of a more preferred embodiment of a container 1 of the invention. The container may be in any configuration but is generally cylindrical and formed out of a single layer of material which forms the collapsible wall 2. The container 1 includes an opening which leads to an open channel 6 which channel 6 includes an abutment 7 which is broken upon the application of force created by formulation 5 being forced from the container. When the abutment 7 is broken the formulation 5 flows to an area adjacent to the flexible porous membrane 3 and is prevented from flowing further in the channel 6 by a non-breakable abutment 8.

Figure 3:
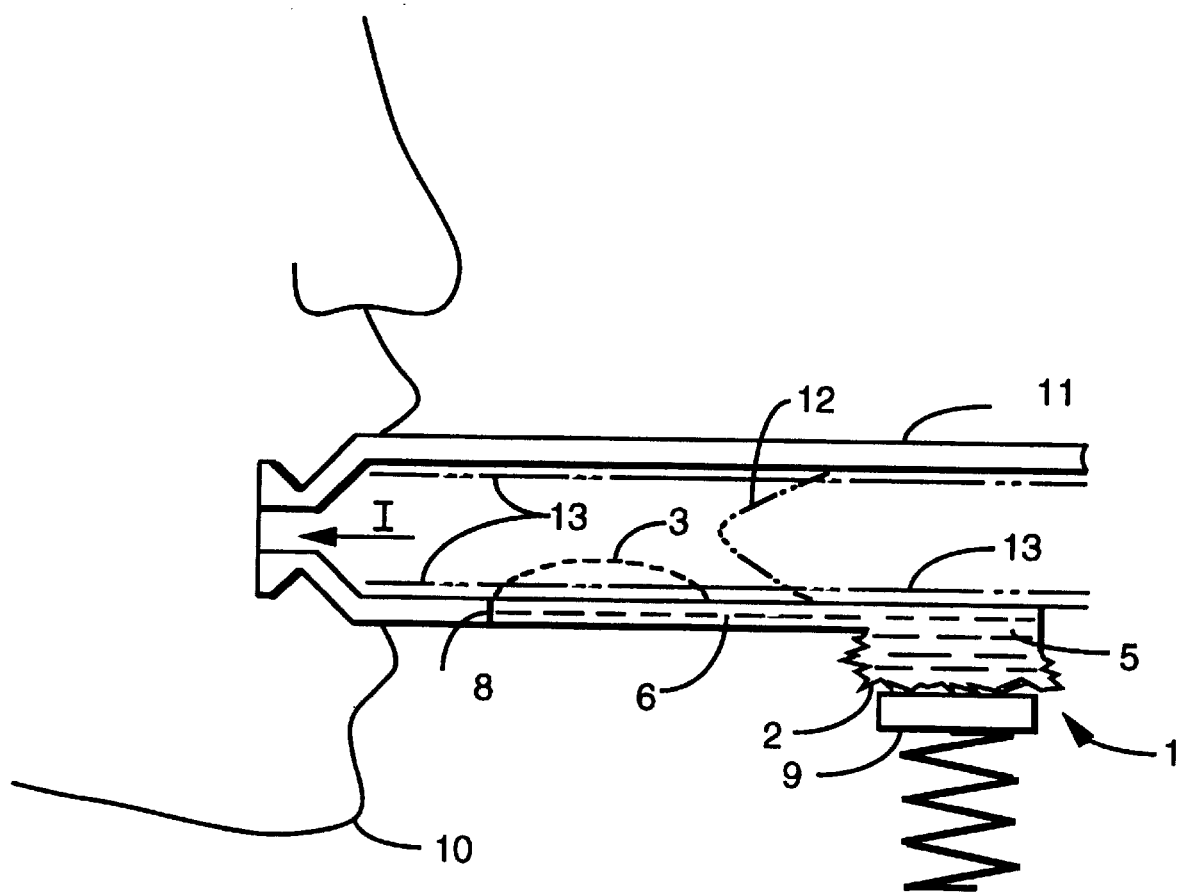
FIG. 3 is a cross-sectional view of the container of FIG. 2 in use in a channel of a drug delivery device.

FIG. 3 is a cross-sectional view of the container 1 of FIG. 2 in use. The wall 2 is being crushed by a mechanical component such as the piston 9 shown in FIG. 3. The piston may be driven by a spring, compressed gas, or a motor connected to gears which translate the electric motor's circle motion to linear motion. The formulation 5 is forced into the open channel 6 (breaking the abutment 7 shown in FIG. 2) and against and through the membrane 3 causing the membrane 3 to protrude outward into a convex configuration as shown in FIG. 3.

The piston 9 has been forced against the container wall 2 after a patient 10 begins inhalation in the direction of the arrow "I". The patient 10 inhales through the mouth from a tubular channel 11. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity right next to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate i.e., 50% or less than the bulk flow rate.

To allow air to flow freely through the channel 11 the upper surface of the flexible porous membrane 3 is substantially flush with (i.e., in substantially the same plane as) the inner surface of the channel 11. Thus, if the membrane 3 remained in place when the formulation 5 move through the pores the formulation would be released into the slow moving or substantially "dead air" below the boundary layer 13. However, the membrane 3 protrudes outward through the boundary layer 13 into the faster moving air. This is desirable in that it aids in avoiding the coagulation of particles. More specifically, when formulation exits the pores the formulation naturally forms spherical particles. Those particles slow down due to the frictional resistance created by the air through which the particles must travel. The particles existing behind them can face reduced air friction because the preceding particle have moved the air aside. Thus later released particles catch up with and merge into the earlier released particles. This can cause a chain reaction resulting in the formation of large particles which can not be readily inhaled into the lung—e.g., the formation of particles having a diameter of more than about 12.0 microns.

Figure 4:
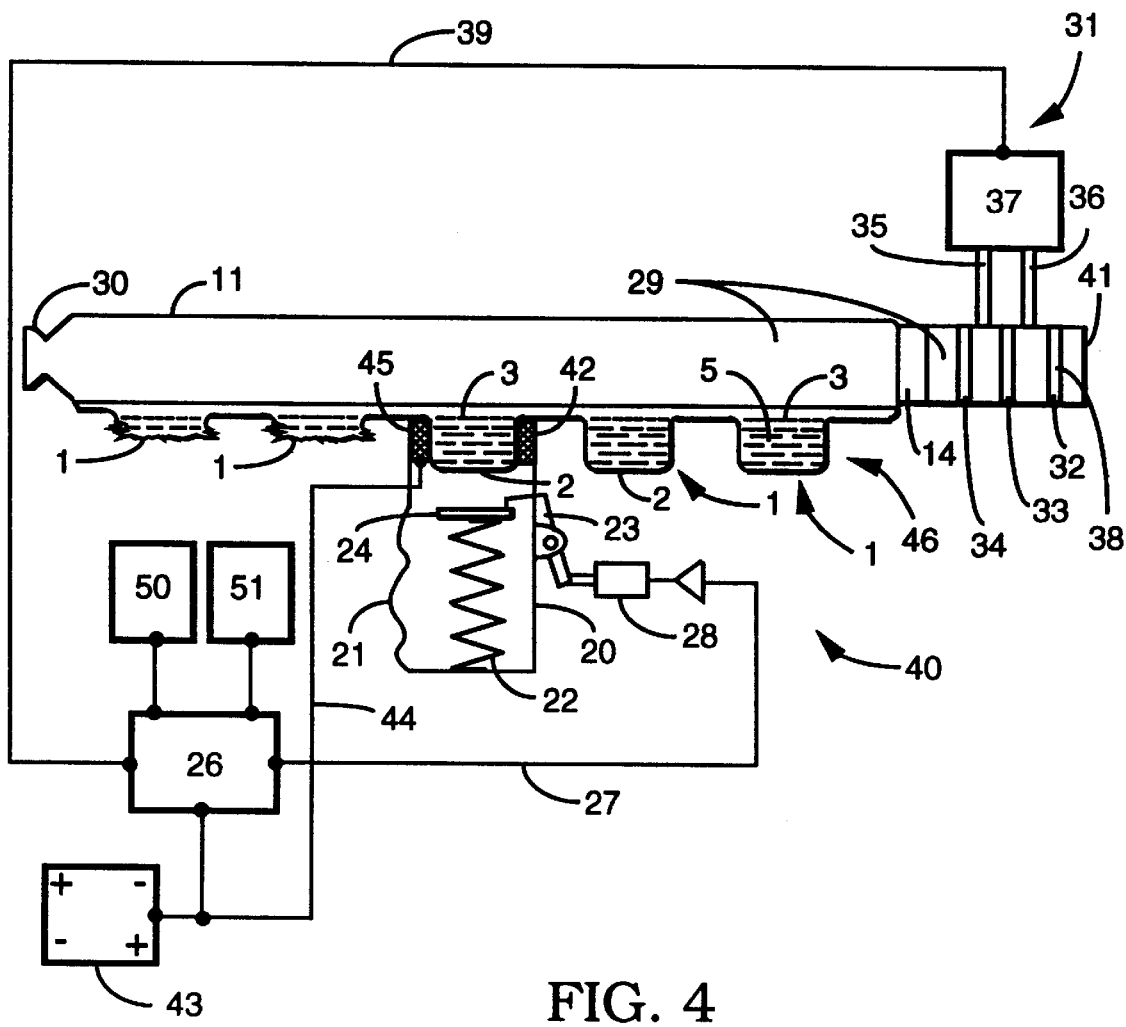
FIG. 4 is a plan view of a drug delivery device of the invention.

A plan view of a simple embodiment of a drug delivery device 40 of the present invention is shown within FIG. 4. The device 40 is loaded and operates with a plurality of interconnected disposable containers 1 which form a package 46. Before describing the details of the individual components of the device 40, a general description of the device and its operation is in order.

Conventional metered dose inhalers and nebulizers suffer from a number of disadvantages. These disadvantages result in the inability to use these devices to repeatedly deliver the same amount of drug to a patient. The disadvantages are due, in part, to the inability to control particle size—especially when the device is used in diverse environments with greatly different humidity conditions or when differing amounts of drug are delivered into a fixed amount of air or similar quantities of drug are delivered into differing amounts of air. By adding sufficient energy to the particles to evaporate any carrier particle size is reduced to a uniform minimum and any humidity variations do not affect particle variability. Further the drug dispensing device of the present invention preferably includes electronic and/or mechanical components which eliminate direct user actuation of drug release. More specifically, the device preferably includes a means for measuring inspiratory flow rate and inspiratory volume and sending an electrical signal as a result of the simultaneous measurement of both (so that drug can be released at the same point each time) and also preferably includes a microprocessor which is programmed to receive, process, analyze and store the electrical signal of the means for measuring flow and upon receipt of signal values within appropriate limits sending an actuation signal to the mechanical means which causes drug to be extruded from the pores of the porous membrane.

The device 40 shown in FIG. 4 is loaded with a disposable package 46. To use the device 40 a patient (see FIG. 3) inhales air from the mouthpiece 30. The air drawn in through the opening 38 (and optionally the desiccator 41) flows through the flow path 29 of the channel 11. The disposable package 46 is comprised of a plurality of disposable containers 1. Each container 1 includes a drug formulation 5 and is covered by the porous membrane 3. An air-heating mechanism 14 located in the flow path 29. The air heating mechanism 14 is preferably positioned such that all or only a portion of the air flowing through the path 29 will pass by the heater, e.g., flow vent flaps can direct any desired portion of air through the heater 14. The heat is preferably turned on for 30 sec or less prior to inhalation and turned off after drug delivery to conserve power.

The device 40 is a hand-held, portable device which is comprised of (a) a device for holding a disposable package with at least one but preferably a number of drug containers, and (b) a mechanical mechanism for forcing the contents of a container (on the package) through a porous membrane. The device preferably further includes (c) a heating mechanism for adding energy to the air flow into which particles are released, (d) a monitor, for analyzing the inspiratory flow of a patient, (e) a switch for automatically releasing or firing the mechanical means after the inspiratory flow rate and/or volume reaches a predetermined point (f) a means for measuring ambient temperature and humidity and (g) a source of power e.g., conventional batteries.

The device for holding the disposable package may be nothing more than a narrow opening created between two outwardly extending bars 42 and 82 or may include additional components such as one or more wheels, sprockets or rollers notably mounted on the end(s) of such bars. The rollers may be spring mounted so as to provide constant pressure against the surface(s) of the package. The device may also include a transport mechanism which may include providing drive power to the roller(s) so that when they are rotated, they move the package from one container to the next. The power source 43 driving the roller(s) is programmed via the microprocessor 26 to rotate the rollers only enough to move the package 39 from one container 1 to the next. In order to use the device 40, the device 40 must be "loaded," i.e. connected to a package 39 which includes drug dosage units having liquid, flowable formulations of pharmaceutically active insulin therein. The entire device 40 is self-contained, light weight (less than 1 kg preferably less than 0.5 kg loaded) and portable. The power source 43 is preferably in the form of standard alkaline batteries. Two 9 volt batteries could supply the heat required to heat the air which contacts the particles by about 20° C. for about 100 doses (see FIGS. 5 and 6 re energy required).

The formulation is preferably heated after the formulation has been forced through the pores of the membrane 3 and aerosolized i.e., energy is preferably added by heating the surrounding air by means of the air-heating mechanism 14 positioned anywhere within the flow path 29. The amount of energy added by the formulation heating mechanism 45 or air-heating mechanism 5 is controlled by the microprocessor 26 based on the amount of formulation in the container 1 and other factors such as the concentration of the insulin in the formulation and surrounding humidity. A hygrometer 50 and thermometer 51 are electrically connected to the microprocessor 26 allowing the amount of heat to be added to be adjusted based on ambient humidity and temperature.

The carrier may be chosen to provide for greater solubility of insulin in the carrier to obtain a high concentration of insulin and thus require less energy to obtain evaporation of the carrier. Droplets having a diameter of 6.3 microns can be formed and subjected to evaporation to obtain a particle of one micron in diameter. In the respiratory tract this one micron particle would be expected to grow to a 3 micron particle due to moisture added from the high humidity environment of the respiratory tract.

Energy for Evaporation

Figure 5:
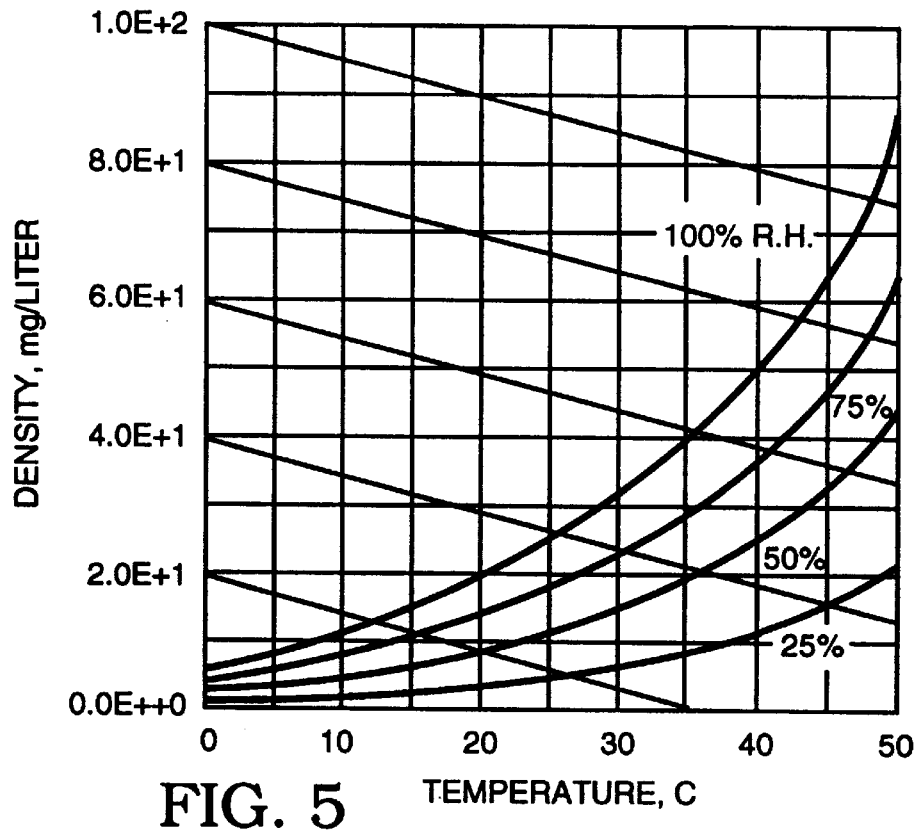
FIG. 5 is a graph plotting the density of water vapor in air versus temperature.

FIG. 5 is a graph which can be used in calculating the amount of energy needed to control the size of delivered droplets by controlling the amount of evaporation of carrier from the aerosolized droplets. The graph of FIG. 5 contains two types of information, the density of evaporated water vs. temperature and relative humidity, and the cooling of the air as the water evaporates. The four lines that show a rapid increase with temperature portray the density of water vapor in air, at 25, 50, 75, and 100% relative humidity. The 100% relative humidity curve represents the maximum number of milligrams of water that can be evaporated per liter of air. The diagonal lines show the temperature change of the air as the water droplets evaporate (hereafter called the air mass trajectory curves). As the evaporation proceeds, the density and temperature will change by moving parallel to these curves. To calculate these curves, air density of 1.185 grams/liter, air specific heat of 0.2401 calories/gram, and water latent heat of vaporization of 0.583 cal/mg were assumed. These values imply that a liter of air will cool 2 celsius degrees for every milligram of water evaporated, i.e. evaporating 10 micro-liters will cool a liter of air 20 celsius degrees.

FIG. 5 can be used to calculate the amount of preheating needed to evaporate all or substantially all of the carrier in the aerosolized particles. As an example, assume the initial ambient conditions are 25° C. and 50% relative humidity. Further, assume that one wants to evaporate 10 μl (10 mgs) of water from an aqueous drug solution. Finally, assume the final relative humidity is 75%. Under these conditions the aqueous carrier would not evaporate completely. More specifically, the final particles would contain approximately equal amounts of drug and water. To calculate the amount of energy to add for this delivery refer to FIG. 5. Locate the point corresponding to 25° C. and 50% relative humidity. Move up by 10 milligrams, the amount of water to be evaporated. Now move to the left until the 75% RH curve is crossed. This occurs at about 29° C. These conditions (75% RH and 29° C.) represent the condition of the air as delivered to the patient. However, still more energy must be added to make up for the cooling of the air as the water evaporates. To calculate this amount of heat, move parallel to the air mass trajectory curves (downward and to the right) until the initial ambient water vapor density is reached, at approximately 47° C. Thus, sufficient heat to warm the air by 22° C. must be added to achieve near complete evaporation.

Figure 6:
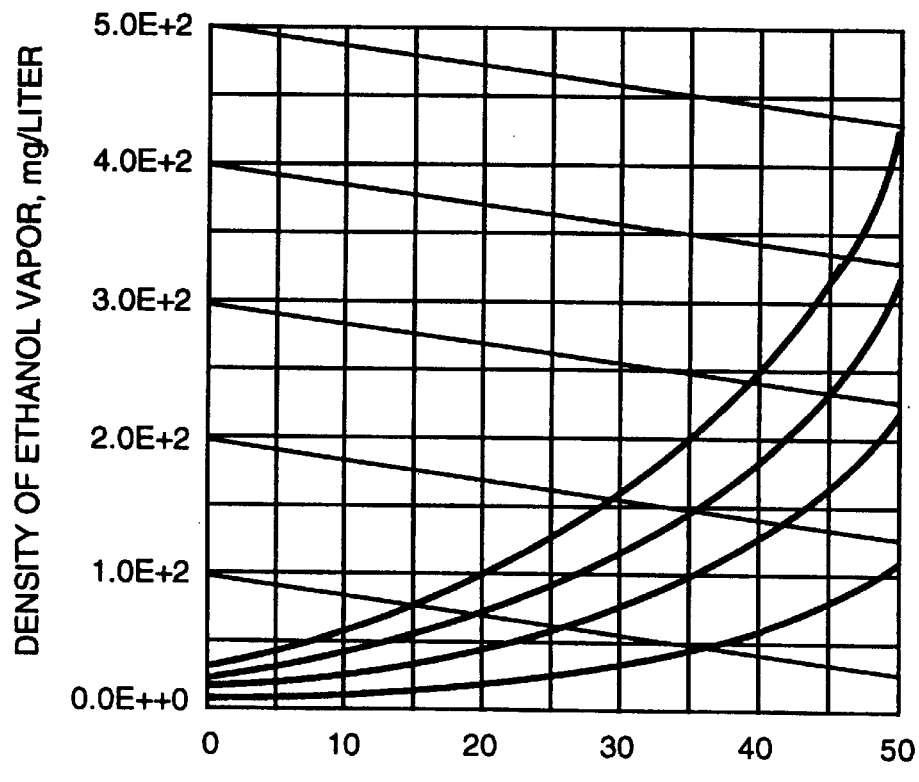
FIG. 6 is a graph plotting the density of ethanol vapor in air versus temperature.

FIG. 6 includes similar information with respect to ethanol which can be used in a similar manner. FIG. 5 shows the density of water vapor in air at 25°, 50° and 75° C. and 100% saturation with the air mass trajectory during evaporation also shown. The same is shown in FIG. 6 for the density of ethanol in air.

The evaporation and growth rates of aqueous droplets is a function of their initial diameter, the amount of drug dissolved therein (concentration) and the ambient relative humidity. The determining factor is whether the water vapor concentration at the surface of the droplet is higher or lower than that of the surrounding air. Because the relative humidity at the surface of a particle (i.e. droplet of aerosolized formulation) is close to 100% for all the low concentration formulations, a five micron droplet will evaporate to a 1 micron dry particle in 0% humidity in less than 20 ms. However, if a particle of drug 1 micron diameter is inhaled into the lungs (99.5% humidity) it can grow to about 3 microns in diameter in approximately one second by accumulating water from the humid lung environment.

Desiccator

The opening 38 may have a desiccator 41 positioned therein which desiccator includes a material which removes water vapor from air being drawn into the flow path 29. By reducing or more preferably eliminating water vapor from the air any water in particles of formulation can be more efficiently evaporated. Further, the particles delivered to the patient will have a smaller and more uniform size whether or not energy is added to cause evaporation of water from the particles of the formulation.

The device may include a mouth piece 30 at the end of the flow path 29. The patient inhales from the mouth piece 30 which causes an inspiratory flow to be measured by flow sensor 31 within the flow path which path may be, and preferably is, in a non-linear flow-pressure relationship. This inspiratory flow causes an air flow transducer 37 to generate a signal. This signal is conveyed to a microprocessor which is able to convert, continuously, the signal from the transducer 37 in the inspiratory flow path 29 to a flow rate in liters per minute. The microprocessor 26 can further integrate this continuous air flow rate signal into a representation of cumulative inspiratory volume. At an appropriate point in the inspiratory cycle, the microprocessor can send a signal to send power from the power source 43 to the air-heating mechanism 14 which uses information from the hygrometer 50, thermometer 51 and particle size and amount of formulation. The microprocessor also sends a signal to an actuator which causes the mechanical means (e.g., the piston 24) to force drug from a container of the package into the inspiratory flow path 29 of the device and ultimately into the patient's lungs. After being released, the drug and carrier will pass through a porous membrane 3 to aerosolize the formulation and thereafter enter the lungs of the patient.

When the formulation 5 includes water as all or part of the carrier it is also desirable to include a desiccator 41 within the flow path 29. The desiccator 41 is preferably located at the initial opening 38 but maybe located elsewhere in the flow path 29 prior to a point in the flow path when the formulation is fired into the flow path in the form of aerosolized particles. By drawing air through the desiccator 41 water vapor within the air is removed in part or completely. Therefore, only dried air is drawn into the remainder of a flow path. Since the air is completely dried water carrier within the aerosolized particles will more readily evaporate. This decreases the energy needs with respect to the heating devices 14. The desiccator material can be any compound which absorbs water vapor from air. For example, it may be a compound selected from the group consisting of $P_2O_5$, $Mg(ClO_4)$, $KOH$, $H_2SO_4$, $NaOH$, $CaO$, $CaCl_2$, $ZnCl_2$, and $CaSO_4$.

Convex/Flexible Porous Membrane

Figure 7:
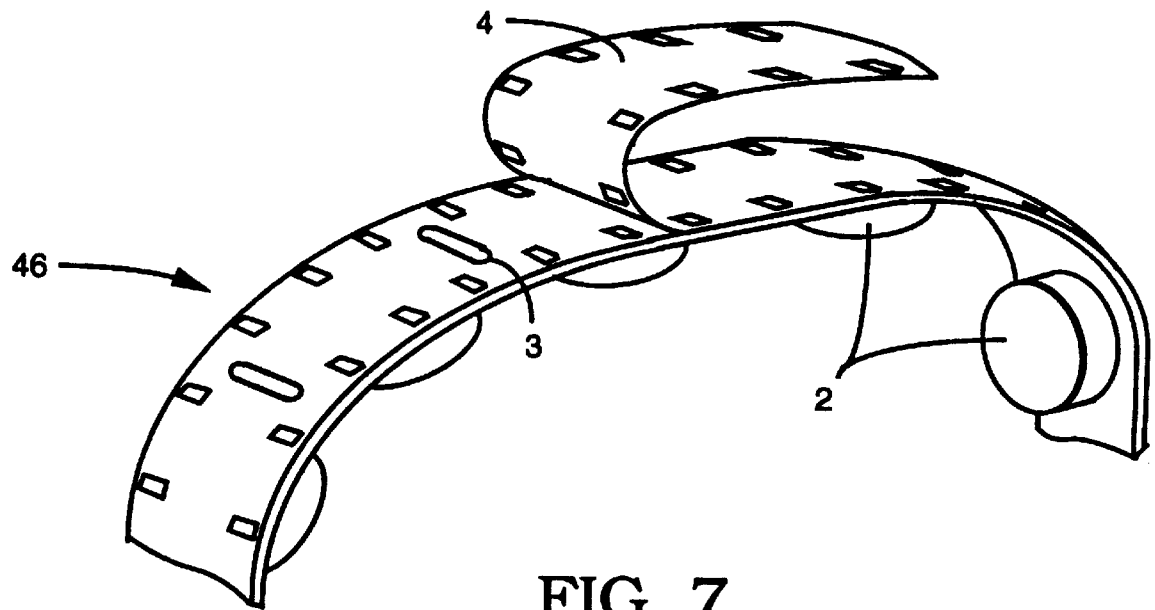
FIG. 7 is a perspective view of the package of the invention.

As shown in FIG. 3 the convex shape that the flexible membrane 3 takes on during use plays an important role. The membrane may be rigid and convex such as the rigid convex membrane 80 shown in FIG. 8. Alternatively, formulation 5 is forced from the container 1 by force applied from a source such as the piston or plate 24 causing the formulation 5 to press against a flexible membrane 3 causing it to convex outward beyond the plan of the resting surface of the membrane 3 and beyond the plan of the inner surface of the channel 11 which is aligned with the surface or membrane 3 when the container 1 is in a drug release position. The convex shape of the membrane 3 is shown in FIG. 3. The convex upward distortion of the membrane is important because it positions the pores of the membrane beyond the boundary layer 13 (shown in FIG. 3) into faster moving air of the channel 29. A number of containers may be connected together to form a package 46 as is shown in FIG. 7. The package 8 is in the form of an elongated tape but can be in any configuration, e.g., circular, square, rectangular, etc.

When pores of the membrane 3 are positioned beyond the boundary layer into the faster moving air of the channel advantages are obtained. Specifically, the (1) formulation exiting the pores is moved to an air stream where it can be readily carried to the patient and (2) the particles formed do not exit into slow moving or "dead" air and thus do not rapidly decelerate to a degree such that particles behind them catch up with, collide into and merge with the particle. Particle collisions are not desirable because they (a) result in particles which are too large and cannot be efficiently inhaled into the lung; and (b) result in an aerosol with diverse and unpredictable particle sizes. Either or both (a) and (b) can result in erratic dosing.

The air-heating mechanism 14 heats the surrounding air within the flow path 29. This causes carrier in the formulation to be evaporated more readily. If sufficient heat is added the only material reaching the patient is the substantially dry insulin drug.

The methodology of the present invention could be carried out with a device that obtains power from a plug-in source. However, the device is preferably a self-contained, hand-held device which is battery powered. Heating mechanisms of various types can be used. For example, see the heating mechanism in the self-contained, portable sealer for plastic colostomy bags in French patent 2,673,142 which is incorporated herein by reference. A portable heater is also taught in European patent applications 0,430,566 A2 for a "Flavor delivering article" and 0,358,002 for "Smoking articles utilizing electric energy," both of which are incorporated herein by reference to disclose and describe heating components powered by batteries.

Supplemental Treatment Methodology

Patients suffering from diabetes mellitus may be treated solely with insulin as indicated above. However, it is possible to treat such patients with a combination of insulin and other drugs such as sulfonylureas which act primarily by stimulating release of insulin from the beta cells in the pancreas. These drugs have the ability of increasing the number of insulin receptors in target tissues and enhance insulin-mediated glucose disposal. Some specific sulfonylurea drugs which can be used in connection with the present invention include acetohexamide administered in an amount of about 500 to 1,500 mg per day; chlorpropamide, administered in an amount of about 50 to 750 mg per day; tolazamide, administered in an amount of about 0.1 to 1 gram per day; tolbutamide, administered in an amount of about 0.5 to 3 grams per day; glipzide administered in an amount of about 2.5 to 40 mg per day and glyburide administered in an amount of about 1.25 to 20 mg per day.

In patients who are producing some insulin, the sulfonylurea drugs may be sufficient to treat the symptoms. Other patients can use a combination of the drugs while administering insulin, while still others require only the administration of insulin. The present invention is beneficial to each type of patient. Further, the present invention allows means for eliminating the need for some patients to take insulin by injection. The patients can be provided with oral doses of sulfonylureas in amounts similar to those indicated above while administering small amounts of insulin via the intrapulmonary route using the device of the present invention. In accordance with one method of the invention, the patient is administered a sulfonylurea drug orally and that treatment is supplemented with insulin administration in relatively small amounts, e.g., five to ten units per dosing event with two to three dosing events per day. Alternatively, the patient is primarily treated by the administration of insulin via the intrapulmonary route and that treatment is supplemented by the oral administration of sulfonylureas of the type described above.

Based on the above, it will be understood by those skilled in the art that a plurality of different treatments and means of administration can be used to treat a single patient. For example, a patient can be simultaneously treated with insulin by injection, insulin via intrapulmonary administration in accordance with the present invention, and sulfonylurea drugs, which are orally administered. Benefits can be obtained by the oral administration of sulfonylurea drugs in that the insulin is naturally released by the patient in a fashion in accordance with real needs related to serum glucose levels. This natural insulin is supplemented by smaller doses provided by intrapulmonary administration in accordance with the present invention. Should such prove to be ineffective for whatever reason, such as breathing difficulties, such could be supplemented by administration via injection.

Drug Delivery Device

The device preferably includes a means for recording a characterization of the inspiratory flow profile for the patient which is possible by including a microprocessor 26 in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

FIG. 4 shows a cross-sectional plan view of a hand held, self-contained, portable, breath-actuated inhaler device 40 of the present invention. The device 40 is shown with a holder 20 having cylindrical side walls and a hand grip 21. The holder 20 is "loaded" in that it includes a container 1. A plurality of containers 1 (2 or more) are preferably linked together to form a package 46.

The embodiment shown in FIG. 4 is a simple version of the invention. The device 40 may be manually actuated and loaded. More specifically, the spring 22 may be compressed by the user until it is forced down below the actuation mechanism 23. When the user pushes the actuation mechanism 23 the spring 22 is released and the mechanical means in the form of a plate 24 is forced upward against a wall 2 of a container 1. Alternatively, a rotating cam (not shown) may be turned by an electric motor to crush the container 1 and force the contents 5 out via a membrane 3. The amount of force applied (and rate of force applied by adjusting the length of piston stroke) can be adjusted to expel all of the contents or, in certain situations, only a portion of the contents e.g., 25%. When the container 1 is compressed its contents are forced out through the membrane 3 and aerosolized and the container and membrane are discarded-not reused. Two additional containers 1 shown to the left are unused. The device of FIG. 4 would not require the use of low boiling point propellants such as low boiling point fluorocarbons. Numerous additional features and advantages of the present invention can be obtained by utilizing the monitoring and electronic components described below.

It is important to note that a variety of devices can be used in order to carry out the methodology of the present invention. However, the device must be capable of aerosolizing a drug formulation in a container and preferably does such by forcing formulation through a porous membrane with the release point based on pre-programmed criteria which may be mechanically set or electronically set via criteria readable by the microprocessor 26. The details of the microprocessor 26 and the details of other drug delivery devices which include a microprocessor and pressure transducer of the type used in connection with the present invention are described and disclosed within U.S. Pat. No. 5,404,871, issued Apr. 11, 1995, entitled "Delivery of Aerosol Medications for Inspiration" which patent is incorporated in its entirety herein by reference, and it is specifically incorporated in order to describe and disclose the microprocessor and program technology used therewith. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, microprocessor 26, containing read only memory which in turn contains the pre-programmed information, is plugged into the device. For each of these three embodiments, changing the programming of the memory device readable by microprocessor 26 will radically change the behavior of the device by causing microprocessor 26 to be programmed in a different manner. This is done to accommodate different drugs for different types of treatment.

Microprocessor 26 sends signals via electrical connection 27 to electrical actuation device 28 which actuates the means 23 which fires the mechanical plate 24 forcing drug formulation in a container 1 to be aerosolized so that an amount of aerosolized drug is delivered into the inspiratory flow path 29 when the flexible membrane 3 protrudes outward through the flow boundary layer. A signal is also sent to the heater 14 to add heat energy to the air in the flow path 29. The device 28 can be a solenoid, motor, or any device for converting electrical to mechanical energy. Further, microprocessor 26 keeps a record of all drug dosing times and amounts using a read/write non-volatile memory which is in turn readable by an external device. Alternatively, the device records the information onto an electronic or magnetic strip on the package 1. The recorded information can be read later by the care-giver to determine the effectiveness of the treatment. In order to allow for ease of use, it is possible to surround the inspiratory flow path 29 with a mouth piece 30.

The electrical actuation means 28 is in electrical connection with the flow sensor 31 which is capable of measuring a flow rate of about 0 to about 800 liters per minute. It should be noted that inhalation flow rates are less than exhalation rates, e.g. max for inhalation 200 lpm and 800 lpm for exhalation. A variety of different types of flow sensors may be used as per U.S. Pat. No. 5,394,866, issued Mar. 7, 1995, U.S. Pat. No. 5,404,871, issued Apr. 11, 1995 and U.S. Pat. No. 5,450,336, issued Sep. 12, 1995, which are incorporated herein by reference. The flow sensor 31 includes screens 32, 33 and 34 which are positioned approximately ¼" apart from each other but may be comprised of a single screen or include a non-linear flow path. It is preferable to include the desiccator 41 at a point prior to the screens 32, 33 and 34 in the flow path so that the elimination of water vapor is considered in any measurement.

As shown in FIG. 4 the flow sensor 31 is made up of a number of components including the transducer 37 and the individual screens 32, 33 and 34. Information from sensor 31 is conveyed via the connecting line 39 to the microprocessor 26. In order to carry out the inhale-exhale maneuver of the invention it is preferable to use the sensor 31 in connection with the microprocessor 26 which can signal the patient that a maximal inhale maneuver and a maximal exhale maneuver has been correctly accomplished. The signal can be an audio signal, visual signal, or both. For example, the device can issue a sound when the device has sensed that a maximal inhale maneuver has been accomplished or flash a green light. If the inhale maneuver was not sensed to be a maximal maneuver the sound will not actuate and the light will not go on or will be a red light. The same is true with respect to the exhale maneuver. The device can be individually set for each patient in that each patient will have a different lung volume and rate at which that lung volume can be inhaled and exhaled. Preferably, the device is individually set by the caregiver. However, devices may be preset for individuals which are judged to have lung volumes of particular sizes e.g., 3 liters, 4 liters, 5 liters, 6 liters in total lung volume. The device can be used to (1) coach a patient to correctly perform the inhale-exhale manuever, (2) deliver drug or (3) both (1) and (2).

Tubes 35 and 36 open to the area between the screens 32, 33 and 34 with the tubes 35 and 36 being connected to a conventional differential pressure transducer 37. Another transducer designed to measure outflow through the opening 38 is also preferably included or the flow sensor 31 is designed so that the same components can measure inflow and outflow. When the user draws air through inspiratory flow path 29, air is passed through the screens 32, 33 and 34 and the air flow can be measured by the differential air pressure transducer 37. Alternatively, other means to measure pressure differential related to air flow, such as a conventional measuring device in the air way, may be used. The flow sensor 31 is in connection with the electrical actuation means 28 (via the connector 39 to the processor 26), and when a threshold value of air flow is reached (as determined by the processor 26), the electrical actuation means 28 fires the release of a mechanical means 23 releasing the plate 24 which forces the release of formulation from a container 1 so that a controlled amount of insulin is delivered to the patient. The microprocessor 26 is optionally connected to an optionally present vibrating device 45 which may be activated.

Vibration Device

The vibration device 45 creates ultrasonic vibrations which are preferably at right angles to the plane of the membrane 3. The device 45 may be in the form of a piezoelectric ceramic crystal or other suitable vibration mechanism. A vibrating device 45 in the form of a piezoelectric crystal may be connected to the porous membrane by means of an attenuator horn or acoustic conduction mechanism, which when correctly matched with the piezoelectric crystal frequency, efficiently transmits ultrasonic oscillations of the piezoelectric crystal to the resonance cavity and the porous polycarbonate membrane and if sized correctly permits the ultrasonic energy to be focused in a polycarbonate membrane 3 allowing for maximum use of the energy towards aerosolizing the liquid formulation 5. The size and shape of the attenuator horn is not of particular importance. It is preferred to maintain a relatively small size in that the device is hand held. The components are chosen based on the particular material used as the porous material, the particular formulation used and with consideration of the velocity of ultrasonic waves through the membrane to achieve a harmonic relationship at the frequency being used.

A high frequency signal generator drives the piezoelectric crystal. This generator is capable of producing a signal having a frequency of from about 575 kilohertz (Khz) to about 32,000 kilohertz, preferably 1,000 to 17,000 kilohertz, more preferably 2,000 to 4,000 kilohertz. The power output required depends upon the amount of liquid being nebulized per unit of time and the area and porosity of the membrane (generally comprised of a polymeric plastic-like material) used for producing the drug dosage unit and/or the efficiency of the connection.

Vibration is applied while the formulation 5 is being forced from the pores of the polycarbonate membrane 3. The formulation can be aerosolized with only vibration i.e., without applying pressure. Alternatively, when vibration is applied in certain conditions the pressure required for forcing the liquid out can be varied depending on the liquid, the size of the pores and the shape of the pores but is generally in the range of about 50 to 600 psi, preferably 100 to 500 psi and may be achieved by using a piston, roller, bellows, a blast of forced compressed gas, or other suitable device. The vibration frequency used and the pressure applied can be varied depending on the viscosity of the liquid being forced out and the diameter and length of the openings or pores.

It is desirable to force formulation through the porous membrane with a relatively low pressure e.g., pressure less than 500 psi in that lower pressure reduces the chance of breaking the membrane during the release of formulation and makes it possible to make a thinner membrane. The thinner membranes make it easier to make small holes in that the holes or pores of the membrane are created using a focussed LASER. It is possible to reduce the pressure further by making the holes conical in cross-section. A LASER with a conical focus is used to burn holes through the membrane. The larger diameter of the conical shape is positioned next to the formulation and the smaller diameter opening is the opening through which the formulation ultimately flows. The ratio of the smaller opening to the diameter of the larger opening is in the range of about 1:2 to about 1:20 i.e., the larger opening is between 2 and 20 times the diameter of the smaller opening. By creating conical openings wherein the smaller end of the cone has a diameter of less than 6 microns it is possible to produce particles which have a diameter of less than 12 microns and it is also possible to force the formulation through the pores using a pressure of less than 500 psi. The small end of the conical opening preferably has a diameter of less than 3 microns for systemic delivery and less than 5 microns for pulmonary delivery and the pressure used for forcing formulation through the pores is preferable less than 350 psi.

Figure 8:
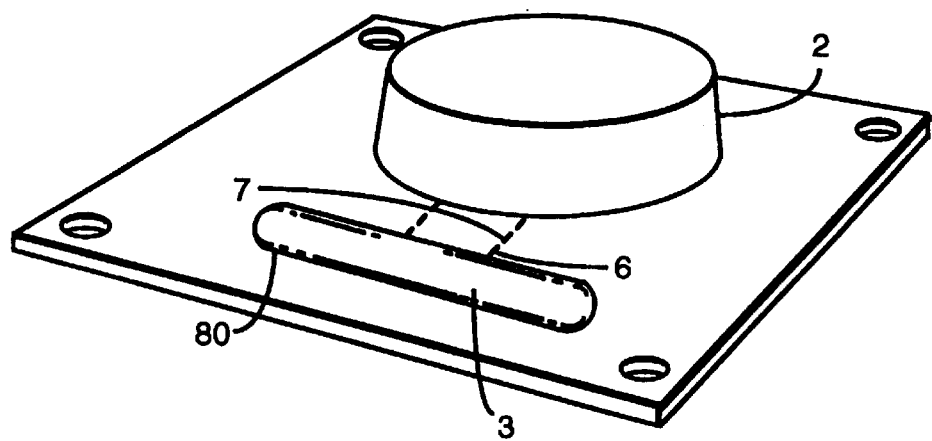
FIG. 8 is a perspective view of a container of the invention.

When small aerosolized particles are forced into the air, the particles encounter substantial frictional resistance. This may cause particles to slow down more quickly than desired and may result in particles colliding into each other and combining, which is undesirable with respect to maintaining the preferred particle size distribution within the aerosol. In order to aid in avoiding the particle collision problem, it is possible to include a means by which air flow and the flexible membrane 3 prevent collisions. Specifically, the patient inhales thereby creating an air flow toward the patient over the protruding membrane 3. The air flow carries the formed particles along and aids in preventing their collision with each other. The shape of the container opening, the shape of the membrane covering that opening, as well as the positioning and angling of the flow of air through the channel 11 relative to the direction of formulation exiting the pores of the membrane 3 can be designed to aid in preventing particle collision. It is desirable to shape the opening and matching membrane so as to minimize the distance between any edge of the opening and the center of the opening. Accordingly, it is not desirable to form a circular opening which would maximize the distance between the outer edges of the circle and the center of the circle, whereas it is desirable to form an elongated narrow rectangular opening covered by a rigid membrane 80 as shown in FIG. 8. Using such a configuration makes it possible to better utilize the air flow relative to all of the particles of formulation being forced form the pores of the membrane 3. When a circular opening is used, particles which are towards the center of the circle may not be carried along by the air being drawn over the membrane 3 and will collide with each other. The elongated rectangle could be formed in a circle, thereby providing an annular opening and air could be forced outward from the outer and inner edges of the circle formed. Further details regarding such are described in U.S. patent application Ser. No. 08/247,012, filed May 20, 1994 (now U.S. Pat. No. 5,544,646 issued Aug. 13, 1996 which is incorporated herein by reference to disclose and describe such.

Operation of the Device 40

The device of FIG. 4 shows all of the components present within the single, hand-held, portable breath actuated device, e.g. the microprocessor 26 and flow sensor 31 used to provide the electronic breath actuated release of drug. The device of FIG. 4 includes a holding means and mechanical means and preferably operates electronically, i.e. the actuation means is preferably not directly released by the user. The patient inhales through inspiratory flow path 29 which can form a mouth piece 30. Air enters the device via the opening 38. The inhaling is carried out in order to obtain a metering event using the differential pressure transducer 37. Further, when the inspiratory flow meets a threshold of a pre-programmed criteria, the microprocessor 26 sends a signal to an actuator release electrical mechanism 28 which actuates the mechanical means 23, thereby releasing a spring 22 and plate 24 or equivalent thereof, forcing aerosolized formulation into the channel 11, and out of the membrane 3 into the flow path 29 where the air surrounding the particles is optionally heated by the air heater 14. Further details regarding microprocessors 26 of FIG. 4 are described within U.S. Pat. No. 5,394,866, issued Mar. 7, 1995, entitled "An Automatic Aerosol Medication Delivery System and Methods", which is incorporated herein by reference in its entirety and specifically incorporated in order to describe and disclose flow measurements, the microprocessor and program technology used therewith.

Microprocessor 26 of FIG. 4 includes an external non-volatile read/write memory subsystem, peripheral devices to support this memory system, reset circuit, a clock oscillator, a data acquisition subsystem and a visual annunciator subsystem. The discrete components are conventional parts which have input and output pins configured in a conventional manner with the connections being made in accordance with instructions provided by the device manufacturers. The microprocessor used in connection with the device of the invention is designed and programmed specifically so as to provide controlled and repeatable amounts of insulin to a patient upon actuation. The microprocessor must have sufficient capacity to make calculations in real time. Adjustments can be made in the program so that when the patient's inspiratory flow profile is changed such is taken into consideration. This can be done by allowing the patient to inhale through the device as a test (monitoring event) in order to measure air flow with preferred drug delivery points determined based on the results of several inhalations by each particular patient. This process can be readily repeated when the inspiratory flow profile is changed for whatever reason. When the patient's lung function has decreased the program will automatically back down in terms of the threshold levels required for release of drug. This "back down" function insures drug delivery to a patient in need but with impaired lung function. Determination of optimal drug delivery points in the inspiratory flow can be done at each dosing event, daily, weekly, or with the replacement of a new cellular array in the device.

The microprocessor 26 of the present invention, along with its associated peripheral devices, can be programmed so as to prevent triggering the actuation mechanism 28 more than a given number of times within a given period of time. This feature makes it possible to prevent overdosing the patient. The overdose prevention feature can be particularly designed with each individual patient in mind or designed with particular groups of patients in mind. For example, the microprocessor can be programmed so as to prevent the release of more than approximately 30 units of insulin per day when the patient is normally dosed with approximately 25 units of insulin drug per day. The device can be designed to switch off this lock-out function so that insulin can be delivered in an emergency situation.

The device can be used as a sensor alone. More specifically, the insulin can be inhaled from a separate device such as from a dry powder inhaler. Thereafter, the sensor portion of the device is made use of in order to perform the inhale-exhale maneuver of the invention. The inhale-exhale maneuver of the invention can be performed a plurality of times at different timed intervals after the delivery of aerosolized insulin. The inhale-exhale manuever can be carried out at anytime after delivery as needed by the patient to reduce glucose levels. In one embodiment the inhale-exhale maneuver is performed at 20 minutes and again at 40 minutes after aerosolized delivery of insulin. However, the maneuver can be performed at 1 minute intervals, 5 minute intervals, 10 minute intervals, 20 minute intervals, or 30 minute intervals after delivery of an aerosolized dose of insulin.

The microprocessor 26 of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices. All of the features of the invention may be provided in a portable, programmable, battery-powered, hand-held device for patient use which has a size which compares favorably with existing metered dose inhaler devices.

The microprocessor 26 of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the electronic actuation means when the inhalation cycle is repeated during the dosing event.

Treatment Via Insulin Analogs

The methodologies of the present invention can be carried out using any type of insulin, although they are preferably carried out using recombinantly produced human insulin. Insulin extracted from animal sources such as bovine or porcine sources can be used. More recently, insulin analogs have been developed. More specifically, novel peptides have been developed wherein the amino acid sequence of the peptides is substantially the same as the amino acid sequence of naturally occurring human insulin but for small changes substituting one amino acid for another. These small changes can have important physiological effects with respect to the treatment of diabetes.

Other general types of insulin analogs are presently used. One type of new analog is sold by Lilly under the name insulin lispro and this analog is absorbed faster after subcutaneous injection. Another type of insulin analog is referred to as superactive insulin. In general, superactive insulin has increased activity over natural human insulin. Accordingly, such insulin can be administered in substantially smaller amounts while obtaining substantially the same effect with respect to reducing serum glucose levels. Another general type of analog is referred to as hepatospecific insulin. Hepatospecific insulin analogs are more active in the liver than in adipose tissue and offer several advantages over currently available insulin therapy. Hepatospecific analogs provide preferential hepatic uptake during peripheral subcutaneous administration, thereby mimicking, more closely, the metabolic balance between the liver and the peripheral tissues. Obtaining the correct metabolic balance is an important part of proper treatment of diabetics and administration via the intrapulmonary route should provide advantages over intermuscular injection with respect to obtaining such a balance. It may be desirable to include mixtures of conventional insulin with insulin lispro or with insulin which is hepatospecific and/or with superactive insulin analogs. Hepatospecific analogs are disclosed and described within published PCT application WO90/12814, published Nov. 1, 1990, which application is incorporated herein by reference for its disclosure of such hepatospecific insulin analogs and in order to disclose other information cited within the other publications referred to within WO90/12814.

U.S. patent application Ser. No. 074,558 discloses a superactive human insulin analog, [10-Aspartic Acid-B] human insulin, which has increased activity over natural human insulin. Specifically, [10-Aspartic Acid-B] human insulin was determined to be 4 to 5 times more potent than natural insulins. U.S. patent application Ser. No. 273,957 and International Application Serial No. PCT/US88/02289 disclose other superactive insulin analogs, des-pentapeptide (B26–B30)-[$Asp^{B10}$, $Tyr^{B25}$-$\alpha$-carboxamide] human insulin, (B26–B30)-[$Glu^{B10}$, $Tyr^{B25}$-$\alpha$-carboxamide] human insulin, and further insulin analogs of the formula des (B26–B30)-[$X^{B10}$, $Tyr^{B25}$-$\alpha$-carboxamide] human insulin, in which X is a residue substituted at position 10 of the B chain. These insulin analogs have potencies anywhere from 11 to 20 times that of natural human insulin. All of the above-described insulin analogs involve amino acid substitutions along the A or B chains of natural human insulin, which increase the potency of the compound or change other properties of the compound.

Other than Lyspro the insulin analogs are not presently used for the treatment of patients on a commercial scale. However, insulin lispro and other insulin analogs being developed could be used with the present invention in that the present invention can be used to provide variable dosing in response to currently measured serum glucose levels. Further, since many insulin analogs are more potent than conventional insulin, their delivery via the intrapulmonary route is particularly convenient.

Method of Administration

The method and device of the invention provides a number of features which make it possible to achieve the controlled and repeatable dosing procedure required for the treating of diabetes (which is life threatening) with insulin. First, the membrane is permanently convex or is flexible and protrudes into fast moving air aiding the elimination of particle collisions. Second, the invention makes it possible to eliminate any carrier from the aerosolized particles solution de either insulin solution droplets or substantial dry insulin particles to a patient which particles can be manufactured to have a uniform size. By delivering particles of uniform size repeatability of dosing is enhanced regardless of the surrounding environment, e.g. different humidity conditions. Third, the device makes it possible to administer drug at the same point with respect to inspiratory flow rate and inspiratory volume at each drug delivery point thereby improving repeatability of dosing.

The method of the invention involves the release of a liquid, flowable insulin formulation from individual disposable containers which may be interconnected in a package. This is desirable in that the liquid, flowable drug is packaged under a sterile environment and therefore does not require and preferably does not include additional materials such as antifungal, bacteriostatics, and preservatives which would normally be required in a liquid formulation if the formulation was to be opened, exposed to air, closed and later used again. A new container and membrane are used for each release of drug. Thus, the membrane and container are disposable thereby preventing clogging of pores which takes place with reuse. The invention does not require the use of low boiling point propellants such as low boiling point fluorocarbons. The use of such low boiling point propellants in conventional metered dose inhaler devices is desirable because such propellants eliminate the need for preservatives, antifungal and bacteriostatic compounds. However, there are potential environmental risks to using low boiling point fluorocarbons. Accordingly, the present invention provides potential environmental benefits and would be particularly useful if government regulations prevented further use of devices which dispensed low boiling point fluorocarbons.

In addition to environmental advantages, the present invention offers advantages due to the relatively slow speed at which the aerosol dispersion is delivered to the patient. A conventional metered dose inhaler device discharges the aerosol outward at a relatively high rate of speed which causes a large amount of the aerosol particles to make contact with the inside of the patient's mouth and the back of the patient's throat. This decreases the amount of drug actually administered to the patient's lungs as compared with the present system, wherein the aerosol is delivered at a relatively slow rate of speed and can be inhaled slowly by the patient.

The method preferably uses a drug delivery device which is not directly actuated by the patient in the sense that no button is pushed nor valve released by the patient applying physical pressure. On the contrary, the device of the invention provides that the actuation mechanism which causes drug to be forced from a container is fired automatically upon receipt of a signal from a microprocessor programmed to send a signal based upon data received from a monitoring device such as an airflow rate monitoring device. A patient using the device withdraws air from a mouthpiece and the inspiratory rate, and calculated inspiratory volume of the patient is measured simultaneously one or more times in a monitoring event which determines an optimal point in an inhalation cycle for the release of a dose of any desired drug. Inspiratory flow is preferably measured and recorded in one or more monitoring events for a given patient in order to develop an inspiratory flow profile for the patient. Recorded information is preferably analyzed by the microprocessor in order to deduce a preferred point within the patient's inspiratory cycle for the release of drug with the preferred point being calculated based on the most likely point to result in a reproducible delivery event.

A flow rate monitoring device continually sends information to the microprocessor, and when the microprocessor determines that the optimal point in the respiratory cycle is reached, the microprocessor actuates a component which fires a mechanical means (and activates the vibration device) which causes drug to be forced out of the container and aerosolized. Accordingly, drug is repeatedly delivered at a pre-programmed place in the inspiratory flow profile of the particular patient which is selected specifically to maximize reproducibility of drug delivery and peripheral deposition of the drug. It is pointed out that the device of the present invention can be used to, and actually does, improve the efficiency of drug delivery. However, this is not the most important feature. A more important feature is the reproducibility of the release of a tightly controlled amount of drug (with a narrow range of particle size) repeatedly at the same particular point in the respiratory cycle so as to assure the delivery of a controlled and repeatable amount of drug to the lungs of each individual patient, i.e. intrapulmonary drug delivery with tightly controlled dosing.

The heating component(s) and/or the desiccator to remove water vapors aid in providing repeatability in dosing in that the particles reaching the patient will have the same size regardless of the surrounding humidity. By keeping the particle size the same at each dosing event the particles deposit at the same general area of the lung at each event. These features improve repeatability along with automatic control of the drug release mechanism, combined with frequent monitoring events in order to calculate the optimal flow rate and time for the release of drug. Further, the particles will have uniform size in that all carrier is removed regardless of the humidity of the surrounding environment. Because the drug release mechanism is fired automatically and not manually, it can be predictably and repeatedly fired at that same point in the inspiratory cycle. Because dosing events are preferably preceded by monitoring events, the point in the inspiratory cycle of the release can be readjusted based on the particular condition of the patient. For example, patients suffering from asthma have a certain degree of pulmonary insufficiency which may well change with the administration of drug. These changes will be taken into account in the monitoring event by the microprocessor which will readjust the point of release of the drug in a manner calculated to provide for the administration of an amount of insulin to the patient presently needed by the patient at each dosing event.

When administering drug using the inhalation device of the present invention, the entire dosing event can involve the administration of anywhere from 10 $\mu$l to 10 ml of drug formulation, but more preferably involves the administration of approximately 50 $\mu$l to 1,000 $\mu$l of drug formulation. Very small amounts of drug (e.g., nanogram amounts) may be dissolved or dispersed within a pharmaceutically acceptable, liquid, excipient material to provide a liquid, flowable formulation which can be readily aerosolized. The container will include the formulation having insulin therein in an amount of about 0.5 unit to 5 units, more preferably about 1 unit. The large variation in the amounts which might be delivered are due to different delivery efficiencies for different devices, formulations and different patients needs.

The entire dosing event may involve several inhalations by the patient with each of the inhalations being provided with drug from the device. For example, the device can be programmed so as to release the contents of a single container or to move from one container to the next on a package of interconnected containers. Delivering smaller amounts from several containers can have advantages. Since only small amounts are delivered from each container and with each inhalation, even a complete failure to deliver drug with a given inhalation is not of great significance and will not seriously disturb the reproducibility of the dosing event. Further, since relatively small amounts are delivered with each inhalation, the patient can safely administer a few additional units of insulin without fear of overdosing.

In addition to drug potency and delivery efficiency, drug sensitivity must be taken into consideration. The present invention makes it possible to vary dosing over time if sensitivity changes and/or if user compliance and/or lung efficiency changes over time.

Based on the above, it will be understood that the dosing or amount of insulin actually released from the device can be changed based on the most immediately prior monitoring event wherein the inspiratory flow of a patient's inhalation is measured.

One of the important features and advantages of the present invention is that the microprocessor can be programmed to take a number of different criteria into consideration with respect to dosing times. For example, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of drug within a given time. For example, the device could be programmed to prevent dispersing more than ten units of insulin within one hour for a patient with low insulin requirements, or more for a patient requiring a large dose of insulin. More importantly, the device can be programmed to take both criteria into consideration. Thus, the device can be programmed to include a minimum time interval between doses and a maximum amount of drug to be released within a given time period. For example, the microprocessor could be programmed to allow the release of a maximum of ten units of insulin during an hour which could only be released in amounts of one unit with each release being separated by a minimum of five minutes.

The dosing program can be designed with some flexibility. For example, if the patient normally requires 25 units per day of insulin, the microprocessor can be programmed to provide a warning after 25 units have been administered within a given day and to continue the warning thereafter to alert the user of possible overdoses. By providing a warning and not a lock-out, the device allows for the patient to administer additional insulin, if needed, due to a decreased lung function, a different diet, and/or account for misdelivery of insulin such as due to coughing or sneezing during an attempted delivery.

The ability to prevent overdosing is a characteristic of the device due to the ability of the device to monitor the amount of insulin released and calculate the approximate amount of insulin delivered to the patient based on monitoring a variety of lung function parameters. The ability of the present device to prevent overdosing is not merely a monitoring system which prevents further manual actuation of a button. As indicated above, the device used in connection with the present invention is not manually actuated, but is fired in response to an electrical signal received from a microprocessor (which received data from a monitoring device such as a device which monitors inspiratory flow) and allows the actuation of the device upon achieving an optimal point in a inspiratory cycle. When using the present invention, each actuation of the device will administer drug to the patient in that the device is fired in response to patient inhalation. More specifically, the preferred embodiment of the device does not allow for the release of insulin merely by the manual actuation of a button to fire a burst of insulin into the air or a container.

A variety of different embodiments of the dispersion device of the invention are contemplated. In accordance with one embodiment it is necessary to carry out manual cocking of the device. This means that energy is stored such as by retracting a spring so that, for example, a piston can be positioned below the drug containing container. In a similar manner a piston connected to a spring can be withdrawn so that when it is released it will force air through the air dispersion vents. Automatic cocking of forced storing systems for both the drug formulation and the air flow may be separate or in one unit. Further, one may be manual whereas the other may be done automatically. In accordance with one embodiment the device is cocked manually but fired automatically and electronically based on monitoring the patients inspiratory flow. The formulation may be physically moved through the porous membrane in a variety of different ways. Formulation may be forced through the membrane by a piston or, without applying force to the formulation, the membrane being vibrated at frequencies sufficient to create an aerosol. A combination of forced extrusion and vibration could be used.

The microprocessor 26 of the present invention preferably includes a timing device. The timing device can be electrically connected with visual display signals as well as audio alarm signals. Although insulin is generally administered as needed the timing device and microprocessor can be programmed so as to allow for a visual or audio signal to be sent to the patient at times when the patient would be normally expected to administer insulin. In addition to indicating the time of administration (preferably by audio signal), the device can indicate the amount of insulin which should be administered by providing a visual display. For example, the audio alarm could sound alerting the patient that insulin should be administered. At the same time, the visual display could indicate "one dosage unit" as the amount of drug (number of containers) to be administered. At this point, a monitoring event could take place. After completion of the monitoring event, administration would proceed and the visual display would continually indicate the remaining amount of insulin which should be administered. After the predetermined dose (indicated number of containers) had been administered, the visual display would indicate that the dosing event had ended. If the patient did not complete the dosing event by administering the stated amount of drug, the patient would be reminded of such by the initiation of another audio signal, followed by a visual display instructing the patient to continue administration.

Additional information regarding dosing insulin can be found within Harrison's—Principles of Internal Medicine (most recent edition) and the Drug Evaluation Manual, 1993 (AMA-Division of Drugs and Toxicology), both of which are published by McGraw Hill Book Company, New York, incorporated herein by reference to disclose conventional information regarding dosing of insulin.

Repeatable Dosing

The device 40 schematically shown within FIG. 4 can be specifically operated as follows. A container 1 is loaded into the device 6. The device is then armed meaning that the piston such as the spring-loaded piston 24 is cocked (i.e., the spring is compressed to a ready position. (The container 1 can be squeezed by a cam rotated by an electric motor). If applicable another piston (not shown) used to compress the liquid formulation in a dual container system is cocked. Further, a container 1 of the package is moved into position and any cover is stripped off of the porous membrane 3. Thereafter, the patient withdraws air from the mouthpiece 30 and the patient's inhalation profile is developed using the microprocessor 26. After the inhalation profile is determined, the microprocessor calculates a point within the inhalation profile at which the drug should be released in order to maximize repeatability of the dosing, e.g. by plotting a curve of breath velocity versus time and determining the point on the curve most likely to provide repeatability of dosing. However, in order to carry out methodology in accordance with the present invention it is not necessary to plot any curve of breath velocity versus time. The device can be set so that the dose will be repeatedly released at approximately the same point with respect to inspiratory flow rate and inspiratory volume. If the device repeatedly fires at the same inspiratory flow rate and inspiratory volume each time the patient will receive substantially the same dose to the lung. Both criteria must be measured and used for firing to obtain repeatability.

The microprocessor of the present invention can be programmed to release drug based on all or any of the following parameters.

(1) Delivery should be at an inspiratory flow rate inside a range of about 0.10 to about 2.0 liters per second (efficiency can be obtained by delivering at a flow rate in a range of 0.2 to about 1.8 liters per second and more preferably 0.15 to 1.7 liters per second). Repeatability of the delivery is obtained by releasing at substantially the same inspiratory flow rate at each drug release.

(2) Delivery should be at a point within a patient's inspiratory volume of about 0.05 to about 2.0 liters (further efficiency of delivery can be obtained by delivering within a range of 0.15 to 0.8 liters and more preferably 0.15 to about 0.4 liters). Repeatability of delivery is obtained by delivering at the same inspiratory volume at each release of drug.

(3) Delivery is improved by providing a system which creates particles for systemic delivery wherein the particles are in the range of about 0.5 to about 12.0 microns, preferably 0.5 to 6 microns and more preferably 0.5 to about 3 microns.

(4) It is desirable to have obtained a concentration of the drug in the carrier in the range of from about 0.01 to about 12.50 preferably 0.1 to 10%. By maintaining the concentration of drug to carrier in this range it is possible to create particles which are somewhat larger than would be desirable for delivery but to reduce those particles in size by evaporation of carrier.

(5) Air drawn into the flow path of the aerosolized particles can be heated by adding energy to each 10 $\mu l$ of formulation in an amount of about 20 Joules to 100 Joules, more preferably 20 Joules to 50 Joules. The heated air aids in reducing the effect of humidity and evaporates carrier away from the particles thereby providing smaller particles for inhalation.

(6) Air is added to the aerosolized formulation by the patient drawing air into the aerosolized mist in an amount of about 50 milliliters to 2 liters per 10 microliters of aerosol formulation.

(7) Vibration may be created on the porous membrane in an amount 575 to 32,000, preferably 1,000 to 17,000 and more preferably 2,000 to 4,000 kilohertz.

(8) The pore size of the membrane is regulated within a range of 0.25 to about 6.0 microns, preferably 0.5 to 3 microns and more preferably 1 to 2 microns. This size refers to the diameter of the pore through which the formulation exits the membrane. The diameter of the opening into which the formulation flows may be 2 to 20 times that size in diameter thereby providing a conical configuration.

(9) The viscosity of the formulation and the membrane porosity affect the amount of pressure which needs to be applied to force the formulation through the pores over a given period of time and the viscosity should be within the range of 25% to 1,000% the viscosity of water.

(10) The extrusion pressure is regulated within a range of 50 to 600 psi more preferably 100 to 500 psi. Lower pressures may be obtained by using the conical configuration for the pore size.

(11) The microprocessor should also be provided information regarding the ambient temperature and atmospheric pressure. The temperature is preferably close to room temperature i.e., within a range of 15° C. to 30° C. An atmospheric pressure is generally 1 atmosphere or slightly lower at higher altitudes, e.g., about 75% of 1 atmosphere.

(12) To provide for consistency in dosing the ratio of the carrier to drug should be maintained constant and more highly concentrated insulin formulation are more desirable.

(13) A desiccator is preferably used to remove water vapor from air drawn into the flow path by the patient.

(14) The pores are preferably placed in the porous membrane in an elongated oval or elongated rectangular configuration. By configuring the pores in this manner and drawing air perpendicularly over the narrower dimension of the configuration it is possible to reduce the amount of collisions between particles and thereby avoid particles collision resulting in accumulation.

(15) The thickness of the membrane is preferably regulated in the range of 5 to 200 microns or more preferably 10 to 50 microns. Thinner membranes are useful in that less pressure is required to force formulation through the membrane. The membrane has a tensile strength of 5,000 to 20,000, preferably 8,000 to 16,000 and more preferably 14,000 to 16,000 psi.

(16) The membrane is configured so as to have a convex configuration which protrudes into faster moving air created by the patient's inhalation or is designed to be flexible so that it will assume a convex configuration when formulation is forced through the membrane.

(17) After the microprocessor is provided information with respect to above parameters or measurements a drug release point is chosen the microprocessor will continually return to substantially the same firing point at each drug delivery so as to obtain repeatability of dosing.

After drug has been delivered it is possible to discontinue any readings with respect to flow and/or volume. However, it is preferable to continue readings with respect to both criteria after drug has been released. By continuing the readings the adequacy of this patient's particular drug delivery maneuver can be determined. All of the events are recorded by the microprocessor. The recorded information can be provided to the caregiver for analysis. For example, the caregiver can determine if the patient correctly carried out the inhalation maneuver in order to correctly delivery drug and can determine if the patient's inhalation profile is effected by the drug.

Monitoring Diabetic Control

All methods of treating diabetes involve measuring glucose levels in some manner. Such measurements are necessary in order to titrate proper dosing and avoid the over-administration of insulin which can result in fatal hypoglycemia. Measurements of urine glucose alone are insufficient to assess diabetic control and bring mean plasma glucose values into a near normal range since the urine will be free of glucose when the plasma concentration is relatively normal. For this reason, "home glucose monitoring" is used in those patients treated by continuous subcutaneous insulin infusion (CSII) or multiple subcutaneous injection (MSI) techniques. Such monitoring requires capillary blood which can be obtained in a substantially painless manner using a small spring-triggered device referred to as Autolet™ produced by Ulstr Scientific Incorporated which device is equipped with small disposable lancelets. The amount of glucose is analyzed using chemically impregnated strips which are read in a commercially available reflectance meter. One commercially available strip is referred to as Chemstrip bG (produced by Bio-Dynamics). The Chemstrip Bg can provide satisfactory values by visual inspection utilizing a dual-color scale, thus eliminating the need for a reflectance meter. Frequent measurement of the plasma glucose (a fairly standard program utilizes seven or eight assays over a 24-hour period) allows a reasonable assessment of mean plasma glucose levels during the day and guides adjustment of insulin dosage.

The methodology of the present invention is preferably utilized in combination with a closely controlled means of monitoring serum glucose levels. More specifically, the drug delivery device of the invention is used to administer doses of insulin via the intrapulmonary route. The doses may be administered in somewhat smaller amounts than are generally administered by injection. The amount of insulin administered can be readily adjusted in that smaller amounts are generally administered using the intrapulmonary delivery methodology of the present invention.

After an aerosolized dose of insulin has been produced and inhaled into the patient's lungs the inhale-exhale maneuver can be performed at any time. Performing the maneuver provides advantages in that it increases the rate at which the insulin enters the circulatory system and thereby makes it possible to more accurately control the amount of additional insulin the patient might need in order to properly adjust the glucose level. If the maneuver is not performed a greater amount of time must pass until the patient is sure that sufficient insulin has not already been absorbed. Regardless of the manner by which the insulin is administered i.e., by injection or inhalation there is some lag time between the administration of a dose of insulin and its effect on the serum glucose level. Thus, regardless of the means of administration and even when the inhale-exhale maneuver is performed some time must be allowed to pass for the glucose level to decrease prior to the administration of additional insulin in order to avoid overdosing. The use of the inhale-exhale maneuver decreases the "lag" time which is already decreased due to intrapulmonary administration as compared to subcutaneous injections. Further, as indicated above, the microprocessor can be programmed to prevent overdoses.

During the day, as insulin is administered, serum glucose levels are frequently monitored. The amount of insulin administered can be dosed based on the monitored serum glucose levels, i.e., as glucose levels increase, the amount of insulin can be increased, and as glucose levels are seen to decrease, the dosing of insulin can be decreased.

Based on the information disclosed herein in combination with what is known about insulin dosing and serum glucose levels, computer readable programs can be readily developed which can be used in connection with the insulin delivery device of the present invention. More specifically, the microprocessor can be programmed so as to deliver precise doses of insulin which correspond to the particular needs of the patient based on serum glucose monitoring information which is supplied to the microprocessor of the device of the invention. Further, the dosing information contained within the microprocessor of the device of the invention can be fed to a separate computer and/or serum glucose monitoring device (preferably portable) in order to calculate the best treatment and dosing schedule for the particular patient.

Insulin Containing Formulations

A variety of different insulin containing formulations can be used in connection with the present invention. The active ingredient within such formulations is insulin which is preferably recombinantly produced human insulin but, as indicated above, may include insulin extracted from animal sources. Further, the insulin may be an insulin analog which is an analog of human insulin which has been recombinantly produced. Although the insulin and/or analog is generally present by itself as the sole active ingredient, the insulin may be present with an additional active ingredient such as a sulfonylurea. However, such sulfonylureas are generally administered separately in order to more closely control dosing and serum glucose levels.

The present invention provides a great deal of flexibility with respect to the types of insulin to be administered. For example, a container can include insulin by itself or insulin in combination with an insulin analog of any type or combinations of different insulin analogs. Further, a package can be created wherein individual containers include different formulations wherein the formulations are designed to achieve a particular effect e.g., fast acting insulin or quick absorbing insulin. The patient along with the care giver and careful monitoring can determine the preferred insulin dosing protocol to be followed for the particular patient.

Regardless of the active ingredient, there are several basic types of insulin formulations which can be used in connection with the present invention. All of the formulations include insulin, preferably with a pharmaceutically acceptable carrier suitable for intrapulmonary administration.

The insulin may be provided as a dry powder by itself, and in accordance with another formulation, the insulin or active ingredient is provided in a solution formulation. The dry powder could be directly inhaled by allowing inhalation only at the same measured inspiratory flow rate and inspiratory volume for each delivery. However, the powder is preferably dissolved in an aqueous solvent to create a solution which is moved through a porous membrane to create an aerosol for inhalation.

Any formulation which makes it possible to produce aerosolized forms of insulin which can be inhaled and delivered to a patient via the intrapulmonary route can be used in connection with the present invention. Specific information regarding formulations (which can be used in connection with aerosolized delivery devices) are described within Remington's Pharmaceutical Sciences, A. R. Gennaro editor (latest edition) Mack Publishing Company. Regarding insulin formulations, it is also useful to note Sciarra et al. [*Journal of Pharmaceutical Sciences*, Vol. 65, No. 4, 1976].

The insulin is preferably included in a solution such as the type of solution which is made commercially available for injection and/or other solutions which are more acceptable for intrapulmonary delivery. When preparing preferred formulations of the invention which provide for the insulin, excipient and solvent, any pharmaceutically acceptable excipient may be used provided it is not toxic in the respiratory tract.

Formulations include insulin dry powder by itself and/or with an excipient. When such a formulation is used, it may be used in combination with a gas propellant which gas propellant is released over a predetermined amount of dried powder which is forced into the air and inhaled by the patient. It is also possible to design the device so that a predetermined amount of dry powder is placed behind a gate. The gate is opened in the same manner as the valve is released so that the same inspiratory flow rate and inspiratory volume is repeatedly obtained. Thereafter, the dry powder is inhaled by the patient and the insulin is delivered. When a solution is used the device of FIG. 4 is used to create an aerosolized form of the solution which can be inhaled by the patient.

Formulations of the invention can include liposomes containing insulin in combination with an amount of alveolar surfactant protein effective to enhance the transport of the liposomes across the pulmonary surface and into the circulatory system of the patient. Such liposomes and formulations containing such are disclosed within U.S. Pat. No. 5,006,343, issued Apr. 9, 1991, which is incorporated herein by reference to disclose liposomes and formulations of liposomes used in intrapulmonary delivery. The formulations and methodology disclosed in U.S. Pat. No. 5,006,343 can be adapted for the application of insulin and included within the delivery device of the present invention in order to provide for effective treatments of diabetic patients.

The terms "insulin" and "insulin analog" have been defined above. With respect to both terms, applicant points out that a variety of commercial insulin formulations are available. Rapidly acting preparations are always indicated in diabetic emergencies and in CSII and MSI programs. Intermediate preparations are used conventional and MSI regimens. It is not possible to delineate precisely the biologic responses to the various preparations because peak effects and duration vary from patient to patient and depend not only on route of administration but on dose. The various insulins are available as rapid (regular, semilente), intermediate (NPH, lente, globin), and long-acing (PZI, ultralente) preparations, although not all manufacturers offer all varieties. Lente and NPH insulin are used in most conventional therapy and are roughly equivalent in biologic effects, although lente appears to be slightly more immunogenic and to mix less well with regular insulin than does NPH.

Preferred Flow Rates/Volumes

FIG. 9 is a two-dimensional graph wherein the inspiratory flow rate is plotted against the inspiratory volume. To determine a drug release point the patient's inspiratory flow rate and inspiratory volume may be simultaneously and separately determined, e.g., measured. The measurement is taken and the information obtained from the measurement provided to a microprocessor which microprocessor is programmed to release drug (1) at the same point relative to inspiratory flow and inspiratory volume at each release of drug and (2) to select that point within prescribed parameters of inspiratory flow rates and inspiratory volumes. In the particular results plotted in FIG. 9 the microprocessor was programmed to release drug in four general areas with respect to the inspiratory flow rate and inspiratory volume parameters. This resulted in data points being plotted in four general areas on the two-dimensional graph of FIG. 9. The four areas are labeled A, B, C and D. In area A (showing solid triangles), the drug was released when the patient's inspiratory flow rate was "slow to medium" (0.10 to 2.0 liters per sec) with an "early" inspiratory volume of 0.15 to 0.8 liters. In area B (showing open triangles), the drug was released at a "slow" inspiratory rate/0.10 to 1.0 liters/sec) and a "late" volume (1.6 to 2.8 liters). In area C (showing solid diamonds), the drug was released at a "fast" inspiratory flow rate (3.5 to 4.5 liters/sec) and a "late" volume. In area D (showing solid circles), the drug was released at a "fast inspiratory flow rate and an "early" inspiratory volume.

The results shown in FIG. 9 were obtained while administering a radioactively labeled drug to a human. After the administration of the drug it was possible to determine not only the amount of drug, but the pattern of drug deposited within the lungs of the patient. Using this information two conclusions were reached. Firstly, it was determined that it is important to simultaneously and separately consider (in real time) both inspiratory flow rate and inspiratory volume when determining the point for drug release for intrapulmonary drug delivery. Changes in either parameter can greatly effect the amount of drug deposited. Thus, when treating a patient the drug should be released at approximately (±10%, preferably ±5% and most preferable as close as possible to the first release point) the same inspiratory flow rate and inspiratory volume each time—going back to the same point each time for the same patient ensures repeatable dosing. In practice the tighter the point is defined the greater the repeatability of dosing. However, if the point is defined to precisely it can be difficult for the patient to obtain that rate/volume point again. Thus, some degree of tolerance is generally applied. Secondly, it was found that within particular ranges with respect to inspiratory flow rate and inspiratory volume it was possible to obtain a consistently high percentage amount of drug deposited in the lung. Such results are shown graphically within the three dimensional graph as shown in FIG. 10.

The third dimension as shown in FIG. 10 (the height of the four columns) indicates the percentage amount of drug deposited based on the total amount of drug released to the patient. The area labeled A clearly showed the highest percentage of drug delivered to the patient based on the amount of drug released. Using this information it was possible to calculate a specific area regarding inspiratory flow rate and inspiratory volume at which it is possible to obtain not only a high degree of repeatability in dosing, but obtain a higher percentage of drug being delivered based on the percentage of drug released. Specifically, it was determined that the drug should be released within inspiratory flow rate range of 0.10 to 2.0 liters per second and at an inspiratory volume in the range of about 0.15 to about 0.80 liters. This range is shown by the rectangularly shaped column of FIG. 11.

In that intrapulmonary drug delivery systems often provide for erratic dosing it is important to provide a method which allows for consistent, repeatable dosing. This is obtained by simultaneously and separately considering both inspiratory flow rate and inspiratory volume in order to define a point by its abscissa and ordinate for optimal delivery to the lung. If both measurements are separately considered the drug can be released anywhere along the abscissa and ordinate scales shown in FIG. 9. Once a point is selected (such as by randomly selecting a point in box A of the graph of FIG. 9) that selected point (with the same coordinants) is used again and again by a given patient to obtain repeatable dosing. If only one parameter is measured (abscissa or ordinate) and drug is released based on that parameter the drug release point is defined by a line on the graph of FIG. 9. When drug is released again the release can be at any point on that line. For example, the inspiratory flow rate (measured horizontally on the abscissa) might be defined by a point. However, the inspiratory volume (which was not measured and/or considered) would be defined only by a vertical line. Thus, subsequent releases would be at different volumes along that vertical line and the dosing would not be consistent. By measuring both inspiratory flow rate on the abscissa and inspiratory volume on the ordinant the coordinants will mark a point for drug release. That point can be found again and again to obtain repeatability in dosing. The same point should be selected each time as closely as possible and within a margin of errors of ±10% with respect to each criteria. The margin for error can be increased and still maintain acceptable levels of repeatable dosing—but the error should keep the drug release point inside the box A of FIG. 9.

Figure 9:
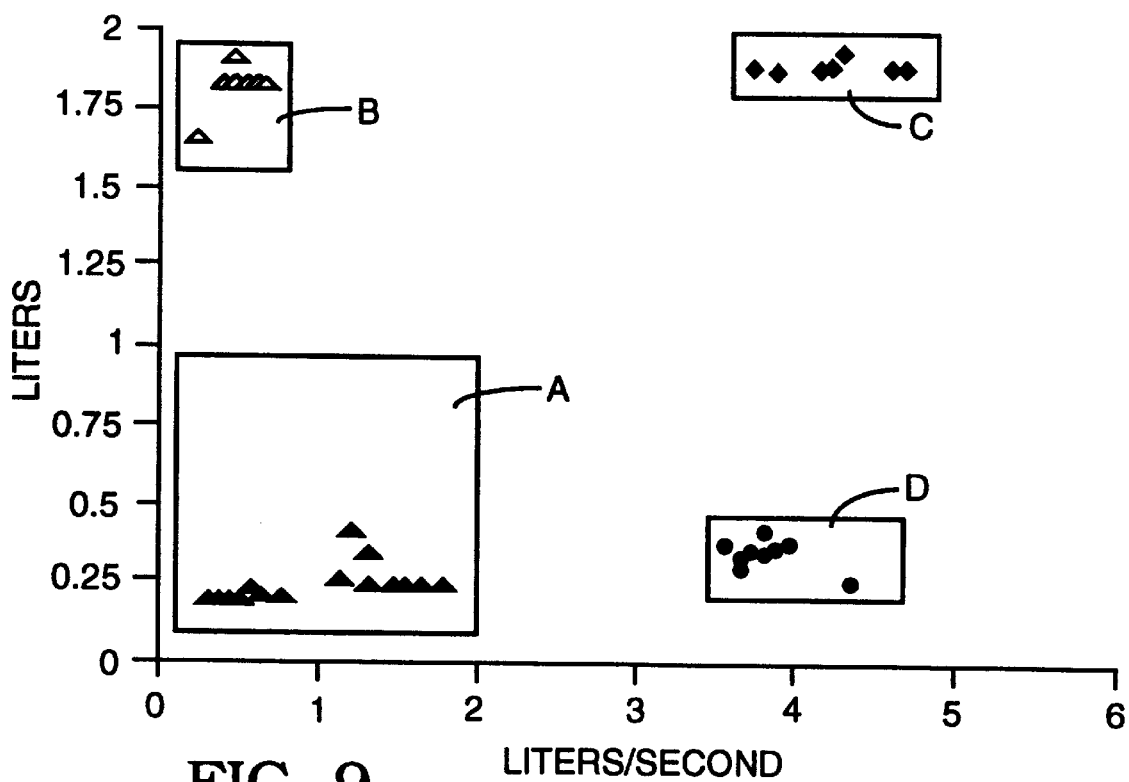
FIG. 9 is a graph showing data points plotted in four general areas with the points plotted relative to inspiratory flow rate (on the abscissa) and inspiratory volume (on the ordinate) in two dimensions.
Figure 10:
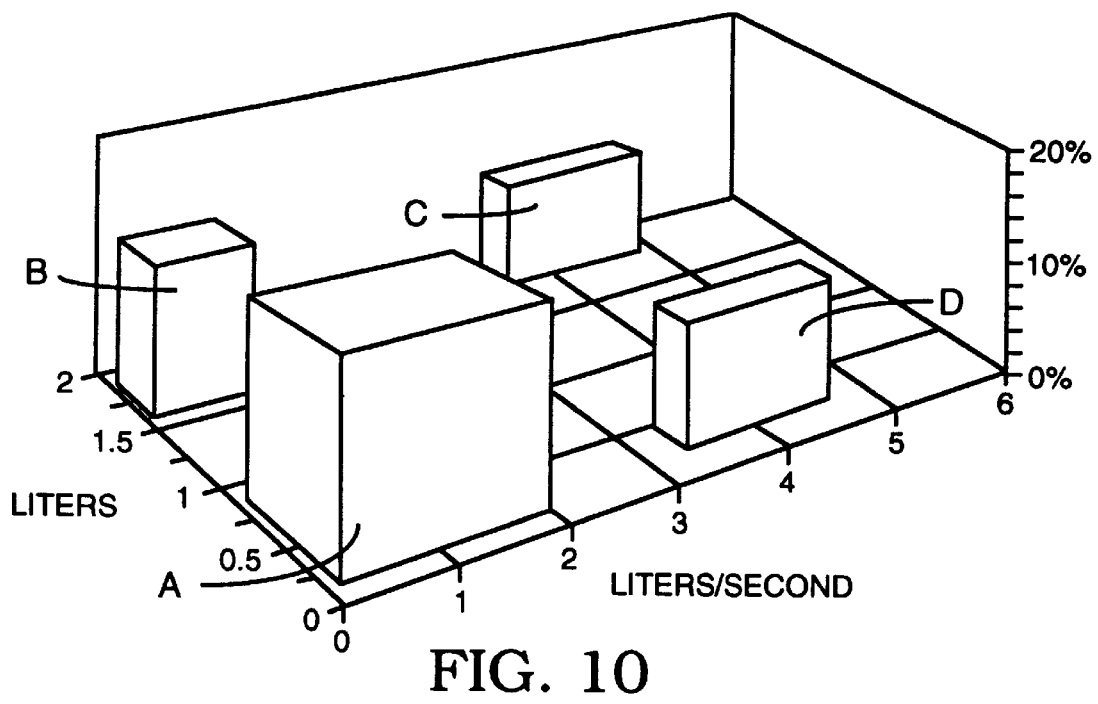
FIG. 10 is a graph showing the four general areas plotted per FIG. 1 now plotted with a third dimension to show the percentage of drug reaching the lungs based on a constant amount of drug released.
Figure 11:
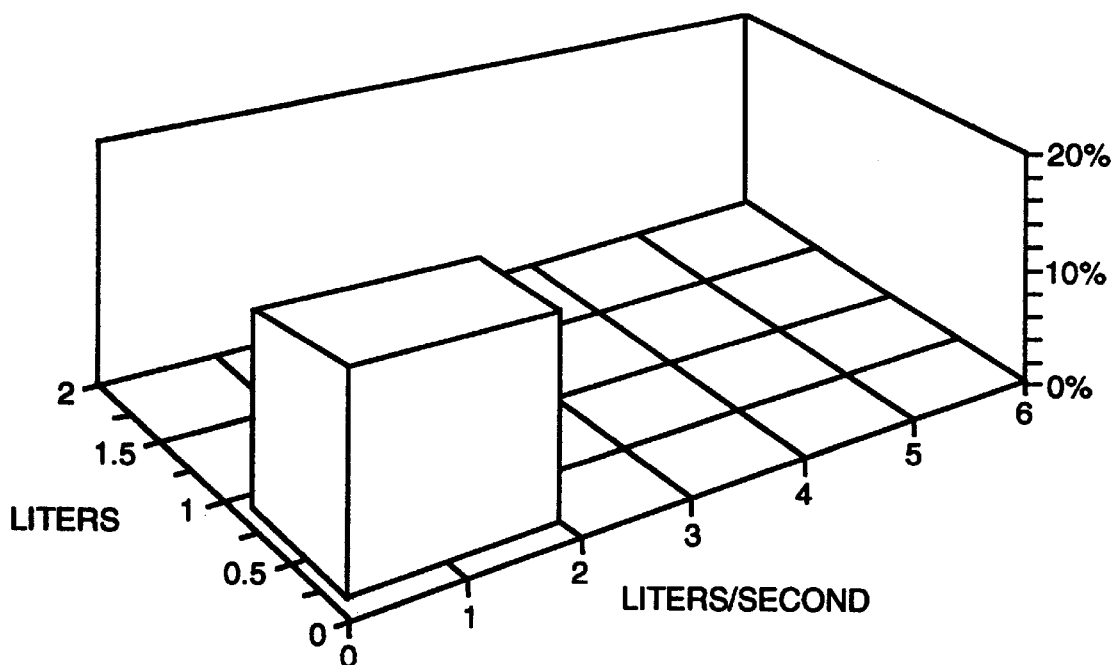
FIG. 11 is a three dimensional graph showing the therapeutic values for inspiratory flow rate and inspiratory volume which provide better drug delivery efficiency.
Figure 12:
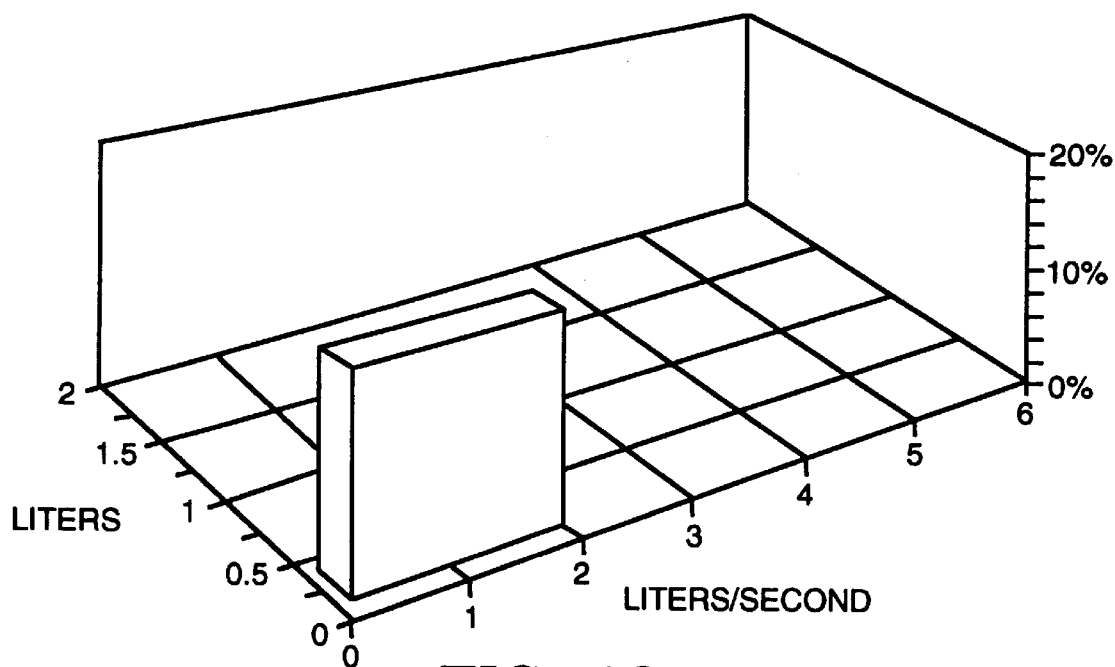
FIG. 12 shows a preferred range of the values shown in FIG. 11.
Figure 13:
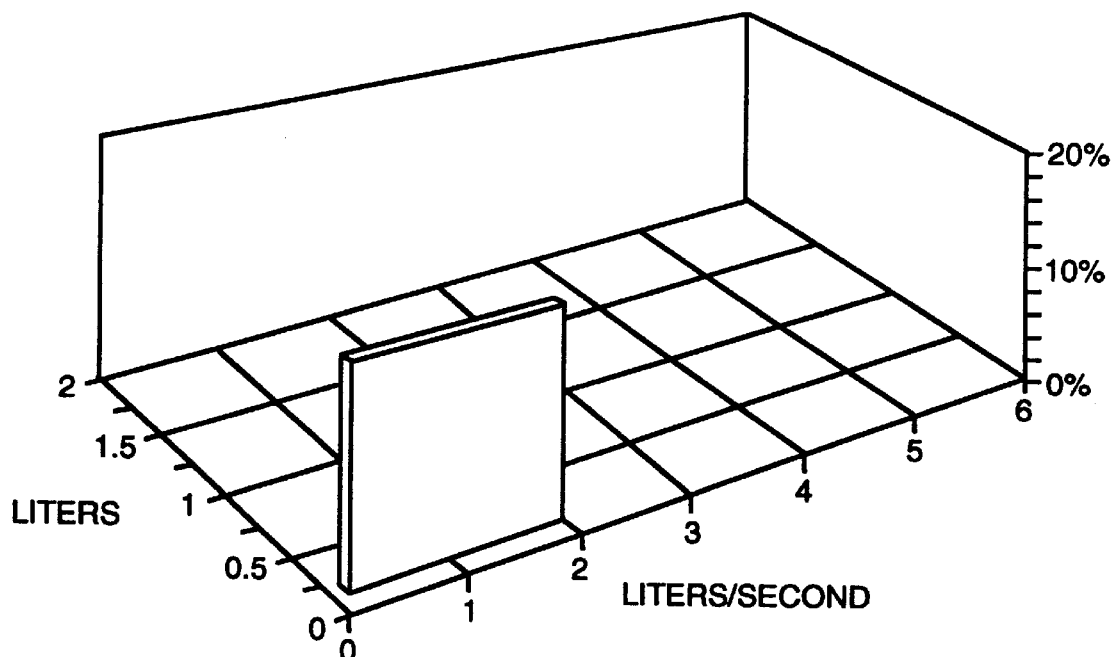
FIG. 13 shows a particularly preferred range for the valves of FIG. 11.
Figure 14:
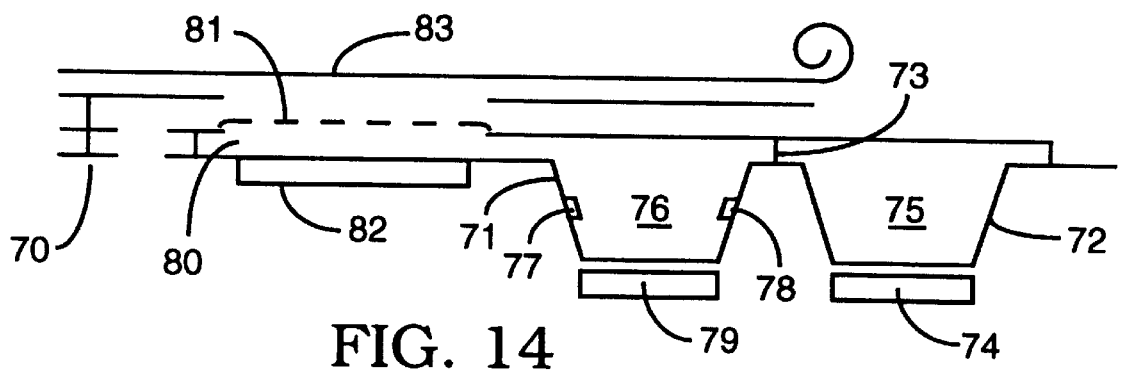
FIG. 14 is a schematic view of a dual compartment insulin formulation container.
Figure 15:
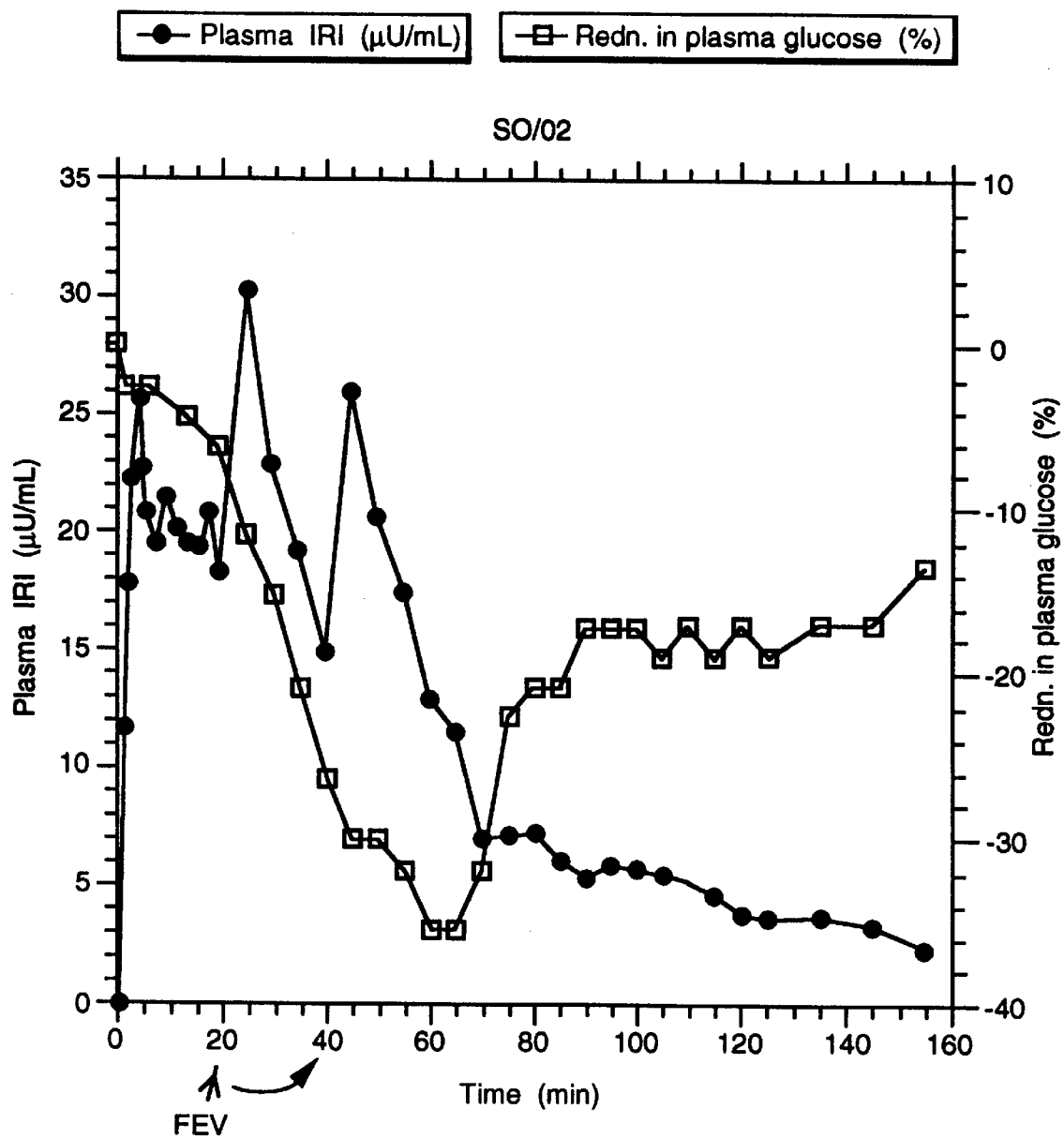
FIG. 15 is a graph plotting the amount of insulin and glucose in plasma over time.

By examining delivery of drug associated with the data points plotted in FIG. 9, it is possible to determine a preferred and particularly preferred and most preferred range as per FIGS. 11, 12 and 13. The preferred range of FIG. 11 shows drug released at a volume of 0.15 to 0.8 liters and rate of 0.10 to 2.0 liters/second. The particularly preferred range plotted in FIG. 12 indicates that the inspiratory flow should be within the range of 0.2 to about 1.8 liters per second with an inspiratory volume in the range of 0.15 to about 0.4 liters. The most preferred range (FIG. 13) is from about 0.15 to about 1.8 liters per second for the inspiratory flow rate and about 0.15 to about 0.25 liters for the inspiratory volume. Thus, preferred delivery can be obtained by (1) repeatedly delivering aerosolized formulation to a patient at the same simultaneously and separately measured inspiratory flow rate and inspiratory volume and (2) releasing drug to the patient within specified therapeutically effective ranges as shown within FIGS. 11, 12 and 13. The invention involves releasing drug (after measuring) inside the ranges as per FIGS. 11, 12 or 13. Thus, the release could begin inside or outside the range. Preferably the drug release begins inside the range and more preferable begins and ends inside the ranges of FIGS. 11, 12 or 13.

The methodology of the invention may be carried out using a portable, hand-held, battery-powered device which uses a microprocessor component as disclosed in U.S. Pat. Nos. 5,404,871, issued Apr. 11, 1995 and 5,450,336, issued Sep. 12, 1995 both of which are incorporated herein by reference. In accordance with another system the methodology of the invention could be carried out using the device, dosage units and system disclosed in U.S. Ser. No. 94/05825 with modifications as described herein. Insulin (which is preferably recombinant insulin) is included in an aqueous formulation which is aerosolized-by moving the formulation through a flexible porous membrane. Alternatively, the methodology of the invention could be carried out using a mechanical (non-electronic) device. Those skilled in the art recognized that various components can be mechanical set to actuate at a given inspiratory flow rate (e.g. a spring biased valve) and at a given volume (e.g. a spinable flywheel which rotates a given amount per a given volume). The components of such devices could be set to allow drug release inside the parameters of FIGS. 11, 12 or 13.

The insulin which is released to the patient may be in a variety of different forms. For example, the insulin may be an aqueous solution of drug, i.e., drug dissolved in water and formed into small particles to create an aerosol which is delivered to the patient. Alternatively, the drug may be in a solution or a suspension wherein a low-boiling point propellant is used as a carrier fluid. In yet, another embodiment the insulin may be in the form of a dry powder which is intermixed with an airflow in order to provide for delivery of drug to the patient. Regardless of the type of drug or the form of the drug formulation, it is preferable to create drug particles having a size in the range of about 0.5 to 12 microns. By creating drug particles which have a relatively narrow range of size, it is possible to further increase the efficiency of the drug delivery system and improve the repeatability of the dosing. Thus, it is preferable that the particles not only have a size in the range of 0.5 to 12 microns but that the mean particle size be within a narrow range so that 80% or more of the particles being delivered to a patient have a particle diameter which is within ±20% of the average particle size, preferably ±10% and more preferably ±5% of the average particle size.

The velocity at which the aerosolized drug is released to the patient is also important in terms of obtaining a high degree of repeatability in dosing and providing for a high percentage of drug being delivered to the patient's lungs. Most preferably, the drug is released from a container in a direction which is normal to the patient's airflow. Accordingly, the drug in a container 1 as shown in FIG. 3 may be released directly upward so that its flow is at a 9° angle with respect to the patient's inspiratory flow which is directly horizontal. After being released, the drug velocity decreases and the drug particles remain suspended for a sufficient period of time to allow the patient's inspiration to draw the drug into the patient's lungs. The velocity of drug released in the direction from the drug release point to the patient may match the patient's inspiratory flow rate but is preferably slower that the patient's inspiratory flow rate and is most preferably about zero. The velocity may be slightly negative, i.e., in a direction away from the patient. The velocity may range from −2.0 liters/sec to 2.0 liters/sec and is preferably zero. It is not desirable to project the drug toward the patient at a rate above the speed of the patient's breath as such may result in drug being deposited on the back of the patient's throat. Thus, the drug release speed should be equal to or less than the breath speed. The actual speed of release can vary depending on factors such as the particle size, the particle composition and the distance between the point of release and the patient. The velocity is preferably such that the particles will (due to air resistance) slow to zero velocity after traveling a distance of about 2 centimeters or less. In general, the shorter the distance required to slow the particles to zero velocity the better.

An aerosol may be created by forcing drug through pores of a membrane which pores have a size in the range of about 0.25 to 6 microns preferably 0.5 to 3.0 microns. When the pores have this size the particles which escape through the pores to create the aerosol will have a diameter about twice the diameter of the pore opening from which the formulation exists. However, the particle size can be substantially reduced by adding heat to the air around the particles and cause evaporation of carrier. Drug particles may be released with an air flow intended to keep the particles within this size range. The creation of small particles may be facilitated by the use of the vibration device which provides a vibration frequency in the range of about 800 to about 4000 kilohertz. Those skilled in the art will recognize that some adjustments can be made in the parameters such as the size of the pores from which drug is released, vibration frequency and amplitude, pressure, and other parameters based on the concentration, density, viscosity and surface tension of the formulation keeping in mind that the object is to provide aerosolized particles having a diameter in the range of about 0.5 to 12 microns.

The drug formulation may be a low viscosity liquid formulation. The viscosity of the drug by itself or in combination with a carrier is not of particular importance except to note that the formulation must have characteristics such that it can be forced out of openings of the flexible or convex membrane to form an aerosol, e.g., using 20 to 400 psi to form an aerosol preferably having a particle size in the range of about 0.5 to 6.0 microns.

Drug may be stored in and/or released from a container of any desired size. In most cases the size of the container is not directly related to the amount of drug being delivered in that most formulations include relatively large amounts of excipient material e.g. water or a saline solution. Accordingly, a given size container could include a wide range of different doses by varying drug concentration.

Drug containers may include indices which may be electronic and may be connected to a power source such as a battery. When the indices are in the form of visually perceivable numbers, letters or any type of symbol capable of conveying information to the patient. Alternatively, the indices may be connected to a power source such as a battery when the indices are in the form of magnetically, optically or electronically recorded information which can be read by a drug dispensing device which in turn provides visual or audio information to the user. The indices can be designed for any desired purpose but in general provides specific information relating to the day and/or time which the drug within a container should be administered to the patient. Such indices may record, store and transfer information to a drug dispensing device regarding the number of doses remaining in the container. The containers may include labeling which can be in any format and could include days of the month or other symbols or numbers in any variation or language.

In addition to disclosing specific information regarding the day and time for drug delivery the indices could provide more detailed information such as the amount of insulin dispensed from each container which might be particularly useful if the containers included different amounts of insulin. Further, magnetic, optical and/or electronic indices could have new information recorded onto them which information could be placed there by the drug dispensing device. For example, a magnetic recording means could receive information from the drug dispensing device indicating the precise time which the insulin was actually administered to the patient. In addition to recording the time of delivery the device could monitor the expected efficacy of the delivery based on factors such as the inspiratory flow rate which occurred following the initial release of insulin. The information recorded could then be read by a separate device, interpreted by the care-giver and used to determine the usefulness of the present treatment methodology. For example, if the glucose levels of the patient did not appear to be responding well but the recorded information indicating that the patient had taken the drug at the wrong time or that the patient had misdelivered drug by changing inspiratory flow rate after initial release it might be determined that further education in patient use of the device was needed but that the present dosing methodology might well be useful. However, if the recordings indicated that the patient had delivered the aerosolized insulin using the proper techniques and still not obtained the correct results (e.g. acceptable glucose levels) another dosing methodology might be recommended. The method of treating Diabetes Mellitus may be carried out using a hand-held, portable device comprised of (a) a device for holding a disposable package comprised of at least one but preferably a number of drug containers, (b) a propellant or a mechanical mechanism for moving the contents of a container through a porous membrane (c) a monitor for analyzing the inspiratory flow, rate and volume of a patient, and (d) a switch for automatically releasing or firing the mechanical means after the inspiratory flow and/or volume reaches a threshold level. The device may also include a transport mechanism to move the package from one container to the next with each container and its porous membrane being disposed of after use. The entire device is self-contained, light weight (less than 1 kg preferably less than 0.5 kg loaded) and portable.

The device may include a mouth piece at the end of the flow path, and the patient inhales from the mouth piece which causes an inspiratory flow to be measured within the flow path which path may be in a non-linear flow-pressure relationship. This inspiratory flow causes an air flow transducer to generate a signal. This signal is conveyed to a microprocessor which is able to convert, continuously, the signal from the transducer in the inspiratory flow path to a flow rate in liters per minute. The microprocessor can further integrate this continuous air flow rate signal into a representation of cumulative inspiratory volume. At an appropriate point in the inspiratory cycle, the microprocessor can send a signal to an actuation means (and/or a vibration device below the resonance cavity). When the actuation means is signaled, it causes the mechanical means (by pressure and/or vibration) to move drug from a container on the package into the inspiratory flow path of the device and ultimately into the patient's lungs. After being released, the drug and carrier will pass through a porous membrane, which can be vibrated to aerosolize the formulation and thereafter the lungs of the patient.

It is important to note that the firing threshold of the device is not based on a single criterion such as the rate of air flow through the device or a specific time after the patient begins inhalation. The firing threshold is based on repeating the firing at the same flow rate and volume as per FIGS. 9–13. This means that the microprocessor controlling the device takes into consideration the instantaneous air flow rate as well as the cumulative inspiratory flow volume. Both are simultaneously considered together in order to determine the optimal point in the patient's inspiratory cycle most preferable in terms of (1) reproducibly delivering the same amount of drug to the patient with each release of drug by releasing drug at the same point each time and maximizing the amount of drug delivered as a percentage of the total amount of drug released by releasing with the parameters described herein.

The device preferably includes a means for recording a characterization of the inspiratory flow profile for the patient which is possible by including a microprocessor in combination with a read/write memory means and a flow measurement transducer. By using such devices, it is possible to change the firing threshold at any time in response to an analysis of the patient's inspiratory flow profile, and it is also possible to record drug dosing events over time. In a particularly preferred embodiment the characterization of the inspiratory flow can be recorded onto a recording means on the disposable package.

The details of a drug delivery device which includes a microprocessor and pressure transducer of the type which may be used in connection with the present invention are described and disclosed within U.S. Pat. Nos. 5,404,871, issued Apr. 11, 1995 and 5,450,336, issued Sep. 12, 1995 incorporated in their entirety herein by reference, and specifically incorporated in order to describe and disclose the microprocessor and program technology used therewith. The pre-programmed information is contained within a nonvolatile memory which can be modified via an external device. In another embodiment, this pre-programmed information is contained within a "read only" memory which can be unplugged from the device and replaced with another memory unit containing different programming information. In yet another embodiment, a microprocessor, containing read only memory which in turn contains the preprogrammed information, is plugged into the device. For each of these embodiments, changing the programming of the memory device readable by a microprocessor will radically change the behavior of the device by causing the microprocessor to be programmed in a different manner. This is done to accommodate different insulin formulation and for different types of treatment, e.g., patients with different types of diabetes.

In a preferred embodiment of the methodology of the invention several different criteria are considered. (1) The inspiratory flow rate and inspiratory volume are simultaneously and separately measured to insure repeatability. (2) The drug is released inside the parameters of FIGS. 11, 12 or 13 with FIG. 13 parameters being most preferred. (3) The particle size of the released drug is in the range of 0.5 to 12 microns and 80% or more and the particles have the same size as the average particle size ±10% in size. (4) The drug particles are released at a velocity which is obtained at a flow rate in the range of greater than −2.0 liters/sec. and less than 2.0 liters/sec. As indicated early the actual velocity can vary based on a number of factors. The release velocity should be determined so that the particles are at or are slowed to zero velocity after traveling about 0.5 to 2 cm from the release point in the absence of patient inhalation. The speed being measured from the drug release point in a direction toward the back of the throat of the patient from the drug release point.

After dosing a patient with insulin it is desirable to measure glucose (invasively or non-invasively) and make adjustments as needed to obtain the desired glucose level. In accordance with all methods the patient does not push a button to release drug. The drug is released automatically by signals from the microprocessor using measurements obtained.

The doses administered are based on an assumption that when interpulmonary delivery methodology is used the efficiency of the delivery is at a known percent amount, e.g., 20% to 50% or more approximately and adjustments in the amount released in order to take into account the efficiency of the device. The differential between the amount of insulin actually released from the device and the amount actually delivered to the patient varies due to a number of factors. In general, devices used with the present invention can have an efficiency as low as 10% and as high as 50% or more meaning that as little as 10% of the released insulin may actually reach the circulatory system of the patient and as much as 50% or more might be delivered. The efficiency of the delivery will vary somewhat from patient to patient and must be taken into account when programming the device for the release of insulin. In general, a conventional metered (propellant-driven) dose inhaling device is about 10% efficient.

One of the important features and advantages of the present invention is that the microprocessor can be programmed to take a variety of different criteria into consideration with respect to dosing times. Specifically, the microprocessor can be programmed so as to include a minimum time interval between doses i.e. after a given delivery another dose cannot be delivered until a given period of time has passed. Secondly, the timing of the device can be programmed so that it is not possible to exceed the administration of a set maximum amount of insulin within a given time. For example, the device could be programmed to prevent dispersing more than 5 units of insulin within one hour. More importantly, the device can be programmed to take both criteria into consideration. Thus, the device can be programmed to include a minimum time interval between doses and a maximum amount of insulin to be released within a given time period. For example, the microprocessor could be programmed to allow the release of a maximum of 5 units of insulin during an hour which could only be released in amounts of 1 unit with each release being separated by a minimum of five minutes.

Additional information regarding dosing with insulin via injection can be found within Harrison's—Principles of Internal Medicine (most recent edition) published by McGraw Hill Book Company, New York, incorporated herein by reference to disclose conventional information regarding dosing insulin via injection.

Another feature of the device is that it may be programmed to not release drug if it does not receive a signal transmitted to it by a transmitter worn by the intended user. Such a system improves the security of the device and prevents misuse by unauthorized users such as children.

The microprocessor of the invention can be connected to external devices permitting external information to be transferred into the microprocessor of the invention and stored within the non-volatile read/write memory available to the microprocessor. The microprocessor of the invention can then change its drug delivery behavior based on this information transferred from external devices such as a glucose monitoring device. All of the features of the invention are provided in a portable, programmable, battery-powered, hand-held device for patient use which has a size which compares favorably with existing metered dose inhaler devices.

Different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation or other source of energy such as from compressed gas or a mechanical device would then cause the dry powder to form a dry dust cloud and be inhaled.

In addition to monitoring glucose levels in order to determine proper insulin dosing, the microprocessor of the present invention is programmed so as to allow for monitoring and recording data from the inspiratory flow monitor without delivering drug. This is done in order to characterize the patient's inspiratory flow profile in a given number of monitoring events, which monitoring events preferably occur prior to dosing events. After carrying out a monitoring event, the preferred point within the inspiratory cycle for drug delivery can be calculated. This calculated point is a function of measured inspiratory flow rate as well as calculated cumulative inspiratory flow volume. This information is stored and used to allow activation of the valve when the inhalation cycle is repeated during the dosing event. Those skilled in the art will also readily recognize that different mechanisms will be necessary in order to deliver different formulations, such as a dry powder without any propellant. A device could be readily designed so as to provide for the mechanical movement of a predetermined amount of dry powder to a given area. The dry powder would be concealed by a gate, which gate would be opened in the same manner described above, i.e., it would be opened when a predetermined flow rate level and cumulative volume have been achieved based on an earlier monitoring event. Patient inhalation would then cause the dry powder to form a dry dust cloud and be inhaled. Dry powder can also be aerosolized by compressed gas, and a solution can be aerosolized by a compressed gas released in a similar manner and then inhaled.

Dual Compartment Container

The dual compartment container 70 of FIG. 14 includes a first container 71 and a second container 72. The containers 71 and 72 are in fluid connection with each other but the fluid connection is interrupted by a membrane 73 which membrane can be ruptured by the application of pressure (preferably in an amount of about 50 psi or less). A device such as the component 74 forces against the bottom of the container 72 and forces the contents 75 (which is liquid) against the membrane 73 which is then ruptured. The liquid 75 then enters the container 71 and mixes with the dry powder insulin 76 present with the container 71. The container 71 may include mixing components 77 and 78. These components may be vibrating devices, ultrasonic devices or other suitable mechanisms allowing for the mixing of the liquid with the dry insulin. When the mixing is completed the component 79 is forced against the container 71 forcing the insulin formulation present therein into the chamber 80. Once the formulation is in the chamber 80 it is there under pressure and can be moved through the flexible membrane 81 by the application of that pressure and/or by the use of a vibrating device 82. The formulation is moved through the membrane 81 only after removal of the cover sheet 83.

The membrane 81 may be permanently convexed or may be flexible and convex outward when the formulation is forced through the membrane and will operate as per the container described in FIGS. 1–4 above. The membrane 81 includes pores having a diameter in the range of about 0.25 micron to about 6 microns and a pore density in the range of $1 \times 10^4$ to about $1 \times 10^8$ pores per square centimeter. The porous membrane 81 is preferably comprised of a material having a density in the range of about 0.25 to 3.0 mg/cm$^2$, more preferably about 1.7 mg/cm$^2$ and a thickness of about 2 to about 20 microns, more preferably 8 to 12 microns. The liquid 75 present in the container 72 is preferably capable of dissolving the insulin. The insulin powder 76 is preferably completely dissolved within the container 71 prior to being forced into the chamber 80. Dissolving the insulin makes it easier to move the insulin through the pores of the membrane 81 and create a fine mist aerosol. Keeping the dried insulin apart from the liquid makes it possible to maintain a longer shelf life.

The instant invention is shown herein in what is considered to be the most practical and preferred embodiments. It is recognized, however, that departures may be made therefrom which are within the scope of the invention and that obvious modifications will occur to one skilled in the art upon reading this disclosure.

We claim:

1. A method of enhancing the rate at which an inhaled drug migrates into a patient's circulatory system, comprising:

aerosolizing a formulation comprised of a monomeric insulin;

inhaling the aerosolized formulation into lungs of a patient and allowing particles of the monomeric insulin to deposit on lung tissue.

2. The method of claim 1, further comprising:

inhaling maximally followed by exhaling the forced vital capacity of the lungs;

wherein the inhaling maximally and exhaling the forced vital capacity are measured.

3. The method of claim 2, wherein the measuring is carried out electronically and a first signal is sent after the inhaling reaches a desired point and a second signal is sent after the exhaling reaches a desired point.

4. The method of claim 1, wherein the formulation is a liquid formulation comprised of a pharmaceutically acceptable carrier and insulin lispro.

5. A method of improving the bioavailability of insulin delivered via the lung, comprising:

aerosolizing a formulation of an insulin analog which analog rapidly disassociates into monomeric form;

inhaling the aerosolized formulation of the insulin analog into the lungs in a manner which allows the particles of the insulin analog to deposit on the lung tissue.

6. The method of claim 5, wherein the inhaled insulin analog is insulin lispro which rapidly disassociates in a monomeric form producing a relative bioavailability greater than twice that seen after the inhalation of a similar amount of recombinant human insulin.

7. A method of reducing sequestration of drug on lung tissue, comprising:

aerosolizing a formulation comprised of a monomeric insulin;

inhaling the aerosolized formulation into lungs of a patient and allowing particles of the monomeric insulin to deposit on lung tissue.

8. The method of claim 7, wherein the monomeric insulin is insulin lispro.

9. The method of claim 7, further comprising:

inhaling maximally followed by exhaling the forced vital capacity of the lungs.

10. The method of claim 9, further comprising:

electronically measuring the inhaling and exhaling.

11. The method of claim 10, further comprising:

sending a first signal after the inhaling reaches a desired point; and sending a second signal after the exhaling reaches a desired point.

12. The method of claim 1, wherein the insulin is insulin lispro.

13. The method of claim 1, further comprising:

inhaling maximally followed by exhaling the forced vital capacity of the lungs.

14. The method of claim 13, further comprising:

electronically measuring the inhaling and exhaling.

15. A method of reproducibly effecting a serum glucose level, comprising:

aerosolizing a formulation comprising monomeric insulin;

administering the aerosolized formulation.

16. The method of claim 15, further comprising:

repeatedly administering the aerosolized formulation at substantially the same inspiratory flow rate and inspiratory volume at each administration.

17. The method of claim 15, wherein the monomeric insulin is insulin lispro.

18. The method of claim 15, further comprising:

monitoring inspiratory flow rate and inspiratory volume; and automatically releasing aerosolized formulation based on a monitored rate and volume.

19. The method of claim 15, further comprising:

inhaling maximally followed by exhaling the forced vital capacity of the lungs.

20. The method of claim 19, further comprising:

measuring the inhaling maximally and exhaling the forced vital capacity.

21. The method of claim 20, wherein the measuring is carried out electronically and a first signal is sent after the inhaling reaches a desired point and a second signal is sent after the exhaling reaches a desired point.

* * * * *

UNITED STATES PATENT AND TRADEMARK OFFICE
CERTIFICATE OF CORRECTION

PATENT NO.     : 5,888,477
DATED          : March 30, 1999
INVENTOR(S)    : Igor Gonda et al.

Page 1 of 1

It is certified that error appears in the above-identified patent and that said Letters Patent is hereby corrected as shown below:

<u>Title page,</u>
Item [75], the inventorship is corrected to include -- Richard D. DiMarchi --.

Signed and Sealed this

Fifth Day of August, 2003

JAMES E. ROGAN
*Director of the United States Patent and Trademark Office*